US012105007B2

(12) United States Patent
Takeda et al.

(10) Patent No.: US 12,105,007 B2
(45) Date of Patent: Oct. 1, 2024

(54) FINE PARTICLE DISPENSING DEVICE, FINE PARTICLE ANALYSIS DEVICE, REACTION DETECTION DEVICE, AND METHOD USING SAID DEVICES

(71) Applicant: ON-CHIP BIOTECHNOLOGIES CO., LTD., Tokyo (JP)

(72) Inventors: Kazuo Takeda, Tokyo (JP); Yuu Fujimura, Tokyo (JP); Masayuki Ishige, Tokyo (JP); Takahide Ino, Tokyo (JP); Yohsuke Bansho, Tokyo (JP); Jin Akagi, Tokyo (JP); Kosuke Osawa, Tokyo (JP)

(73) Assignee: On-Chip Biotechnologies Co., Ltd., Tokyo (JP)

( * ) Notice: Subject to any disclaimer, the term of this patent is extended or adjusted under 35 U.S.C. 154(b) by 647 days.

(21) Appl. No.: 16/333,528

(22) PCT Filed: Sep. 15, 2017

(86) PCT No.: PCT/JP2017/033551
§ 371 (c)(1),
(2) Date: Jun. 28, 2019

(87) PCT Pub. No.: WO2018/052137
PCT Pub. Date: Mar. 22, 2018

(65) Prior Publication Data
US 2019/0339189 A1 Nov. 7, 2019

(30) Foreign Application Priority Data
Sep. 16, 2016 (JP) .................................. 2016-181447

(51) Int. Cl.
*G01N 15/1404* (2024.01)
*B01L 3/02* (2006.01)
(Continued)

(52) U.S. Cl.
CPC .......... *G01N 15/1404* (2013.01); *B01L 3/021* (2013.01); *G01N 15/1433* (2024.01); *B01L 2200/0636* (2013.01)

(58) Field of Classification Search
None
See application file for complete search history.

(56) References Cited

U.S. PATENT DOCUMENTS

| 3,710,933 A | 1/1973 | Fulwyler et al. |
| 3,826,364 A | 7/1974 | Bonner |

(Continued)

FOREIGN PATENT DOCUMENTS

| JP | 7308311 | 11/1995 |
| JP | 11295323 | 10/1999 |

(Continued)

OTHER PUBLICATIONS

Tsutomu, Honma et al, Reaction Apparatus and Reaction Method, 2008, Espacenet English Translation (Year: 2008).*

(Continued)

*Primary Examiner* — Matthew D Krcha
*Assistant Examiner* — Brittany I Fisher
(74) *Attorney, Agent, or Firm* — Heslin Rothenberg Farley & Mesiti P.C.; Jacquelyn A. Graff, Esq.

(57) ABSTRACT

The object of the present invention is to provide a technique for dispensing cells as single cells. The above problem can be solved by an apparatus for dispensing particles comprising a transparent hollow pipette for dispensing sample liquid containing particles, and an image capturing means, wherein the devise has means for capturing two or more images of the dispensing liquid in the hollow pipette; means for comparing two or more shot images, distinguishing a moved particle-like substance from an unmoved particle-like substance in the image-captured particle-like substances, and (Continued)

identifying the moved particle-like substance as a suspended particle; and means for dispensing a sample liquid containing a target number of suspended particles.

7 Claims, 14 Drawing Sheets

(51) Int. Cl.
*G01N 15/10* (2024.01)
*G01N 15/14* (2024.01)
*G01N 15/1433* (2024.01)
*G01N 15/1434* (2024.01)
*G01N 15/149* (2024.01)
*C12Q 1/68* (2018.01)
*C12Q 1/686* (2018.01)

(56) References Cited

U.S. PATENT DOCUMENTS

| | | | |
|---|---|---|---|
| 5,934,278 | A | 8/1999 | Ishihara |
| 6,238,626 | B1 | 5/2001 | Higuchi |
| 7,968,287 | B2 | 6/2011 | Griffiths |
| 8,248,604 | B2 | 8/2012 | Takeda |
| 8,834,793 | B2 | 9/2014 | Koltay et al. |
| 2005/0136528 | A1 | 6/2005 | Bahnson |
| 2009/0042737 | A1 | 2/2009 | Katz |
| 2010/0110177 | A1 | 5/2010 | Yamada |
| 2011/0271746 | A1 | 11/2011 | Shinoda |
| 2011/0294139 | A1 | 12/2011 | Takeda |
| 2012/0288920 | A1 | 11/2012 | Takeda |
| 2013/0037623 | A1 | 2/2013 | Yamaguchi |
| 2013/0095469 | A1 | 4/2013 | Koltay et al. |
| 2013/0288254 | A1 | 10/2013 | Pollack |
| 2014/0087412 | A1 | 3/2014 | Fouras |
| 2015/0367346 | A1 | 12/2015 | Foster et al. |
| 2016/0202281 | A1 | 7/2016 | Fang et al. |

FOREIGN PATENT DOCUMENTS

| | | |
|---|---|---|
| JP | 2004337091 | 12/2004 |
| JP | 2008290027 | 12/2008 |
| JP | 2010535511 | 11/2010 |
| JP | 2011521228 | 7/2011 |
| JP | WO2011086990 | 7/2011 |
| JP | 2011237201 | 11/2011 |
| JP | 5382852 | 1/2014 |
| JP | 2015158489 | 9/2015 |
| JP | 2016521350 | 7/2016 |
| WO | 1998010267 | 3/1998 |
| WO | 1998022625 | 5/1998 |
| WO | 2008132995 | 11/2008 |
| WO | 2009021215 | 2/2009 |
| WO | 2009151858 | 12/2009 |
| WO | 2011099287 | 8/2011 |
| WO | 2014144789 | 9/2014 |

OTHER PUBLICATIONS

Mitani et al., "Rapid SNP diagnostics using asymmetric isothermal amplification and a new mismatch-suppression technology," Nature Methods, vol. 4(3), pp. 257-262, Mar. 2007.

Okada et al., "Mobile Automatic Detection System for Bacillus anthracis using Electrochemical DNA Chip," Biosensors & Bioelectronics, vol. 3, Issue 4, 1000126, pp. 1-4, 2012.

Translation of International Search Report and Written Opinion of the International Searching Authority for PCT/JP2017/033551, Dec. 19, 2017, 16 pages.

Foreign Patent Document No. 2 (JP 2016-521350), A machine translation obtained from Google Patents of this reference has been submitted herewith. Further, Applicant notes that International Publication No. WO 2014/144789 is the English equivalent to JP 2016-5213500.

\* cited by examiner

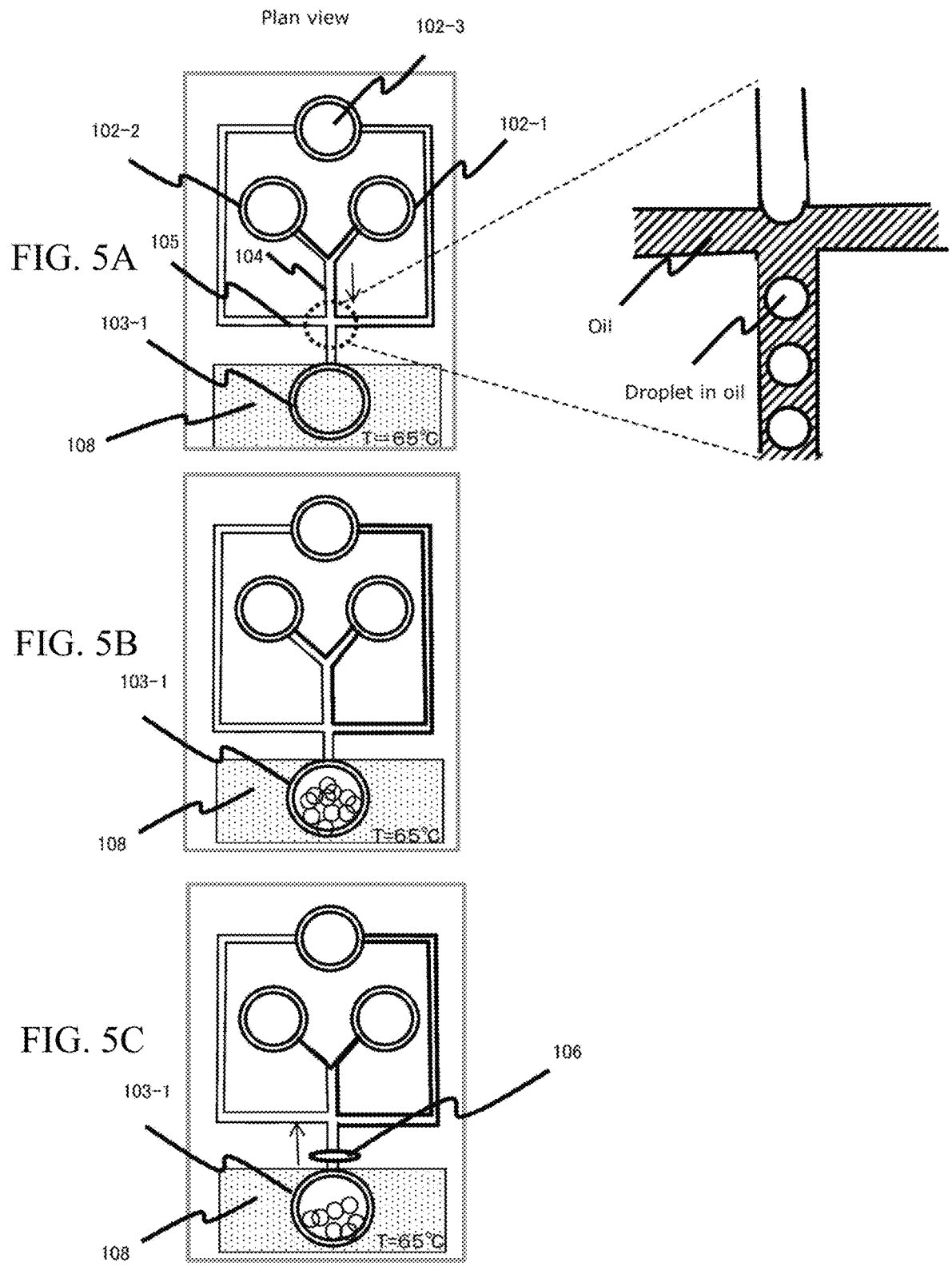

Emulsion formation

Emulsion backflow

FINE PARTICLE DISPENSING DEVICE, FINE PARTICLE ANALYSIS DEVICE, REACTION DETECTION DEVICE, AND METHOD USING SAID DEVICES

CROSS REFERENCE TO RELATED APPLICATIONS

This application is a national stage filing under section 371 of International Application No. PCT/JP2017/033551, filed on Sep. 15, 2017 and published as WO/2018/052137, which claims priority to Japanese Application No. 2016-181447, filed Sep. 16, 2016. The entire contents of each application are incorporated herein by reference in their entireties.

TECHNICAL FIELD

The present invention relates to an apparatus for dispensing particles, an apparatus for analyzing particles, and a reaction detector, and methods using the same.

BACKGROUND ART

In cancer research, it has become important to analyze specific cells in various cell populations one by one. For example, in the development of therapeutic agents for cancer immunotherapy, it is important that immune cells recognize cancer cells as non-self cells. This study requires analysis of the expression profiles of various proteins in cancer cells. This expression profile analysis requires a single cell dispensing technology.

First, the prior art necessary for the single cell dispensing technique will be explained. For example, cell sorter technologies for sorting specific cells among contaminating cells are involved. The cell sorter separates and concentrates the target cells, but has an analysis function as a flow cytometer to identify the target cells. The technology of a flow cytometer is described in Patent literature 1.

Patent literature 2 describes a method for separating cells or particles used in a conventional cell sorter. The method includes discharging liquid droplets of a sample liquid from a nozzle for droplet formation into the air, and separating the liquid droplets which include the cells to be separated using an electric field by giving an electric charge. Patent literature 4 describes a contamination-free technique of a flow cytometer using the disposable micro-flow path cartridge, which is most suitable for regenerative medicine. Patent literature 5 describes a method for separating cells in the disposable micro-flow path cartridge. Furthermore, Patent literature 6 discloses an improved method in which an influence of flow in the micro-flow path is reduced.

A stirring technique for preventing clogging of cells in a flow path when cells are flowed through a micro flow path will be described. Patent literature 11 describes a technique of rotating a propeller to stirrer a cell suspension in a sample reservoir connected to a micro flow path.

Next, conventional techniques for dispensing cells will be explained. Patent literature 7 discloses a technique wherein cells are picked up by a hollow pipette and moved to a different location, and then dispensed by being discharged. Patent literature 8 discloses a technique wherein each of the liquid droplets is delivered by drops through pressure pulse drive using a piezoelectric element and dispensed, after detecting a presence or absence of the cells by image recognition. Further, Patent literature 10 discloses a dispensing method wherein a dispensing head is disposable. Patent literature 14 describes a technique in which the dispensing head is replaceable, the presence or absence of cells is confirmed by image recognition, and the cells are dispensed in units of droplets.

In the conventional technology for sequentially performing a plurality of different processes including sample processing and detection at different times in the interchangeable micro flow path cartridge, a mechanism for stopping the flow is required in the flow path. That is, it is not a technology that requires no said mechanism. For disposable, replaceable cartridges, technology that does not incorporate a special mechanism is advantageous for mass production of the cartridges. All of the conventional techniques require a special mechanism. The following techniques have been reported as conventional techniques for performing multiple processes to detect genes in a micro flow path. Okada et al. (Non-Patent literature 1) reports a method in which a valve and a pump installed in a flow path are used to control a sample flow in different processes. A method of controlling the flow of droplets in oil in a micro flow path using an electric field is described in US20130288254 (Patent literature 12). As a method of gene amplification reaction, Patent literature 9 discloses a digital PCR technique in which PCR reaction spaces are subdivided by using emulsions. As for the method of amplifying DNAs isothermally, a method of performing isothermal amplification reactions in a micro flow path is described in Patent literature 13, and a technique related to a SmartAmp method is described in Non-Patent literature 2.

CITATION LIST

Patent Literature

[Patent literature 1] U.S. Pat. No. 3,710,933
[Patent literature 2] U.S. Pat. No. 3,826,364
[Patent literature 3] WO98/10267
[Patent literature 4] U.S. Pat. No. 8,248,604
[Patent literature 5] Japanese Patent No. 5382852
[Patent literature 6] WO2011/086990
[Patent literature 7] U.S. Patent Application Publication No. 2005/0136528
[Patent literature 8] U.S. Pat. No. 8,834,793
[Patent literature 9] U.S. Pat. No. 7,968,287
[Patent literature 10] Japanese Unexamined Patent Publication (Kokai) No. 11-295323
[Patent literature 11] U.S. Patent Application Publication No. 20150367346
[Patent literature 12] U.S. Patent Application Publication No. 20130288254
[Patent literature 13] WO1998/022625
[Patent literature 14] Japanese Unexamined Patent Publication (Kokai) No. 2015-158489

Non-Patent Literature

[Non-patent literature 1] J Biosens Bioelectron, 2012 (U.S.A.) Vol. 3, 4th edition, 1000126
[Non-patent literature 2] Nature Methods, 2007 (England) Vol. 4, p. 257-262

SUMMARY OF INVENTION

Technical Problem

The challenges in the technique to dispense cells as single cells are: confirmation that the number of cells to be dispensed is one, cell damage, bacterial contamination, and cross contamination between different samples. Patent literature 7 describes a technique in which cells are aspirated by a hollow pipette, moved to a different location, discharged, and dispensed, but it is not a technique in which cells are dispensed one by one. Patent literature 8 discloses a technique wherein each of the liquid droplets is delivered by drops through pressure pulse drive using a piezoelectric element and dispensed, after detecting a presence or absence of the cells by image recognition. However, since it is not possible to exchange the entire flow path system in contact with the sample solution for each sample solution, it is undeniable that the cells after dispensing may be cells carried over from different sample solutions. This is a problem that leads to misdiagnosis between medical samples of different patients. The hollow pipette for dispensing is a hollow container through which the dispensing solution passes before dispensing, and means the part at the tip of the dispensing channel, which will be called the dispensing pipette below.

The present inventors have investigated a method using image recognition to dispense a single cell. However, when the number of cells in the dispensing pipette was attempted to be measured from the image, it was found that it was difficult to distinguish scratches or attached foreign matter of the dispensing pipette from the cells. That is, when the number of cells in the dispensing pipette is measured by image recognition, it is difficult to distinguish the scratches of the dispensing pipette from the cell, and thus the number of recognized cells and the number of dispensed cells do not coincide with each other. Therefore, it has been found that there is a need for a technique for distinguishing between cells and scratches on the dispensing pipette. In addition, with regard to cell damage, when the dispensing operation is performed for a long time, the cell may be damaged. That is, cells are damaged by prolonged exposure of the cells to atmospheric atmospheres that are not in the presence of a $CO_2$ of about 5% suitable for cell growth. This cell damage depends on the type of cell. With regard to bacterial contamination, if the flow path in the dispensing device that contacts the cells is a fixed flow path, bacterial contamination occurs because bacteria grow in the flow path. Buffers containing preservatives may be used to prevent bacterial contamination. However, preservatives may result in cell damage. Further, in the case of the fixed flow path, there is a problem that cross contamination occurs between samples.

Therefore, an object of the present invention is to provide a single cell dispensing technology which is contamination and damage free.

As a preliminary step for single cell dispensing, it is preferable to sort the target cells from the various cell populations. For this purpose, cell sorting in a disposable, interchangeable micro flow path cartridge is preferred. The disposable, interchangeable micro flow path cartridges are useful for medical diagnostic flow cytometers or cell sorters where contamination between samples is a problem. The present inventors use a micro flow path cartridge, and have found the following. That is, a micro flow path having a small cross-sectional area tends to cause clogging of the flow path due to cell accumulation on the bottom of the sample reservoir or cell adsorption on the side surface of the flow path. In order to solve this problem, Patent literature 11 discloses a technique for preventing cells from being deposited by gravity sedimentation on the bottom of a sample reservoir, and for flowing a constant cell concentration to a micro flow path. Although this technology has the effect of preventing cell clogging, it cannot remove clogged cells.

Therefore, an object of the present invention to provide a technique for preventing or removing cells clogged in the flow path of the micro flow path cartridge, and further to improve a technique for purifying and analyzing target cells for single cell dispensing from the various cell populations.

The merit of the interchangeable micro flow path cartridge is that, in addition to contamination-free, the device can be miniaturized by storing the entire flow path system in a small cartridge. In this case, it may be possible to analyze the sample obtained at the clinical site, on the spot. However, in the analysis of a target cell, gene or the like, the clinical sample contains many contaminants which are obstacles to the analysis. Thus, a pretreatment is necessary to detect a gene of interest with high sensitivity. In order to detect genes with high sensitivity even in the presence of high concentrations of contaminants, there is a detection method using droplets in oil, such as digital PCR. However, in order to carry out this method in the disposable, interchangeable micro flow path cartridge, it is necessary to perform different reactions sequentially while flowing the sample liquid, that is, it is necessary to perform multiple processes with different processing times with the same flow path cartridge. At present, as a technology for sequentially performing a plurality of different processes including a treatment and detection of sample in the interchangeable micro flow path cartridge, there is a technology of incorporating a control element in the flow path. However, technology that does not require control elements has not been developed. In the technique described in Non-Patent literature 1, a plurality of processes is performed using a technique in which a control element is incorporated.

For example, in the conventional products of digital PCR (Bio-Rad or Raindance Technologies) using water-in-oil emulsion droplets, three processes of emulsion formation, gene amplification reaction, and analysis are carried out. However, each process is performed on different devices and cannot be performed by one device Accordingly, an object of the present invention to provide a technique for sequentially performing a plurality of different processes including treatment and detection of a sample in an interchangeable micro flow path cartridge.

Solution to Problem

The present inventors have conducted intensive studies into the technique of dispensing cells as single cells. As a result, the present inventors surprisingly found that scratches or attached foreign matter of the dispensing pipette from cells can be easily distinguished from movable suspended cells, by capturing two or more images of a dispensing liquid in the hollow pipette, and distinguishing a moved particle-like substance from an unmoved particle-like substance in the image-captured particle-like substances, to identify the moved particle-like substance as a suspended particle. Particles that do not move include, in addition to the scratches and attached foreign matter of the dispensing pipette, cells that should be dispensed but that do not move due to adhesion. The adhered cells are undispensed and should not be counted as dispensed cells. Therefore, there is no problem in uncounting all non-moving particles.

Further, the present inventors have conducted intensive studies into the technique for preventing or removing cells clogged in the flow path of the micro flow path cartridge. As a result, the present inventors surprisingly found that the cells clogged in the flow path of the micro flow path cartridge can be prevented or removed by making the pressure in the sheath reservoir higher than the pressure of the sample reservoir, and flowing back the sheath fluid in the sheath reservoir to the sample reservoir, in the micro flow path cartridge (sometimes referred to as micro flow path chip).

Furthermore, the present inventors have conducted intensive studies into the technique for sequentially performing a plurality of different processes including treatment and detection of a sample in an interchangeable micro flow path cartridge. As a result, the present inventors surprisingly found that a plurality of different processes including treatment and detection of a sample in an interchangeable micro flow path cartridge can be sequentially performed by forming a droplet from a mixture of sample and reagent by using oil, reacting the sample in the droplet reservoir, and detecting the reaction.

The present invention is based on the above findings.

Namely, the present invention relates to:

[1] an apparatus for dispensing particles comprising a transparent hollow pipette for dispensing sample liquid containing particles, and an image capturing means, wherein the devise has means for capturing two or more images of the dispensing liquid in the hollow pipette; means for comparing two or more shot images, distinguishing a moved particle-like substance from an unmoved particle-like substance in the image-captured particle-like substances, and identifying the moved particle-like substance as a suspended particle; and means for dispensing a sample liquid containing a target number of suspended particles,

[2] the apparatus for dispensing particles according to item [1], further comprising means for forcibly moving the dispensing liquid in the hollow pipette,

[3] The apparatus for dispensing particles according to item [1] or [2], further comprising means capable of controlling the gas atmosphere to a carbon dioxide gas atmosphere of 0.03 to 50%,

[4] the device for dispensing particles according to any one of items [1] to [3], wherein data of the number of dispensed particles is recorded by storing particle images in the hollow pipette just before dispensing,

[5] the apparatus for dispensing particles according to any one of items [1] to [4], comprising a preparatory dispensing chamber for supplying the sample liquid from an upper of the hollow pipette to the hollow pipette,

[6] a method for dispensing particles, using a device for dispensing particles comprising a transparent hollow pipette for dispensing sample liquid containing particles, and an image capturing means, comprising the steps of: (1) capturing two or more images of a dispensing liquid in the hollow pipette, (2) comparing two or more shot images, and distinguishing a moved particle-like substance from an unmoved particle-like substance in the image-captured particle-like substances, to identify the moved particle-like substance as a suspended particle; and (3) dispensing a sample liquid containing a target number of suspended particles,

[7] the method for dispensing particles according to items [6], wherein the device for dispensing particles further comprises means for forcibly moving the dispensing liquid in the hollow pipette, and the dispensing liquid in the hollow pipette is image-captured two or more, before and after the dispensing liquid is moved by means for forcibly moving the dispensing liquid in the image-capturing step (1),

[8] the method for dispensing particles according to item [6] or [7], wherein the device for dispensing particles further comprises means capable of controlling the gas atmosphere to a carbon dioxide gas atmosphere of 0.03 to 50%, and the steps (1) to (3) are performed in a 3-10% carbon dioxide gas atmosphere,

[9] the method for dispensing particles according to any one of items [6] to [8], wherein the steps (1) to (3) are performed after a plurality of dispensable amounts of sample liquid are aspirated into a preparatory dispensing chamber located on the hollow pipette before the image-capturing step (1) and a certain amount of sample liquid is supplied to the hollow pipette from the preparatory dispensing chamber, so as to sequentially dispensing the dispensing liquid,

[10] an apparatus for analyzing particles comprising: a flow path cartridge in which a flow path is formed in a transparent substrate, an illumination unit configured to illuminate particles in a sample liquid flowing through the flow path, a detection unit configured to detect particles of interest by detecting scattered light or fluorescence generated from the particles when the particle is illuminated, and identifying the particle based on its signal intensity, wherein a sample reservoir connected to a first flow path;

a sheath reservoir to which a second flow path and a third flow path joined from the left and right sides of the first flow path are connected; and a discharged liquid reservoir connected to a downstream side of the first flow path after joining; are formed on the cartridge, and wherein the apparatus has a means for flowing back a sheath fluid in the sheath reservoir to the sample reservoir by making the pressure in the sheath reservoir higher than the pressure in the sample reservoir

[11] the apparatus for sorting particles, wherein the apparatus for analyzing particles according to item [10] further comprises a force generating unit configured to apply a force for changing a flow direction to the particles based on the signal from the detection unit,

[12] the apparatus for sorting particles according to item [11], wherein the flow path cartridge has a fourth branched flow path and a fifth branched flow path which are oppositely connected to both sides of the first flow path in which the second flow path and the third flow path are joined; and a sorting reservoir connected to the fourth branched flow path and a collection reservoir connected to fifth branched flow path; and wherein the force generating unit generates a pulse flow flowing in the direction from the fourth branched flow path to the fifth branched flow path so as to sort the particles into the collection reservoir by changing the flow of particles in the direction of the fifth branch flow path,

[13] A method for preventing or removing a particles clogged in the flow path, using the apparatus for analyzing particles according to item [10] or the apparatus for sorting particles according to item [11] or [12], wherein the pressure in the sheath reservoir is made higher than the pressure in the sample reservoir, and the sheath fluid in the sheath reservoir flows back to the sample reservoir, to prevent or remove the particles clogged in the flow path from the sample reservoir,

[14] A reaction detector for reacting sample liquid in micro flow path cartridge and detecting the result of the reaction, comprising a sample reservoir, a reagent reservoir, an oil reservoir, and a droplet reservoir, wherein a first flow path from the sample reservoir and a second flow path from the reagent reservoir join to form a third flow path, a fourth flow path and a fifth flow path from the oil reservoir join the third flow path from both sides thereof, the third flow path is connected to the droplet reservoir downstream of the junction of the fourth flow path and the fifth flow path, the reaction detector has a means for flowing back droplets in oil formed at the junction, which are flowed into the droplet reservoir, through the third flow path, and has a means for detecting the reaction in the third flow path,

[15] the reaction detector according to item [14], wherein the means for flowing back the droplets causes a pressure applied to the droplet reservoir to be higher than a pressure applied to the sample reservoir, the reagent reservoir, and the oil reservoir,

[16] the reaction detector according to item [14] or [15], wherein the reaction is a gene amplification reaction, the reaction detector has a means for controlling a temperature of the droplet reservoir, and the means for detecting the reaction detects fluorescence due to light irradiation,

[17] the reaction detector according to any one of items [14] to [16], wherein the sample reservoir and the reagent reservoir are a single sample reagent reservoir, and the first flow path and the second flow path are a single third flow path from the sample reagent reservoir,

[18] a method for detecting reaction using the reaction detector according to any one of claims 14 to 17, comprising the steps of (1) forming a droplet in oil by supplying oil to a mixture of sample and reagent from both sides of the third flow path through the fourth flow path and the fifth flow path, (2) reacting the sample in the droplet, and (3) detecting the reaction of the sample in the droplet,

[19] the method for detecting reaction according to item [18], wherein the sample reaction is detected after flowing back the droplet from the droplet reservoir to the third flow path in the detection step (3),

[20] the method for detecting reaction according to item [18] or [19], wherein the reaction is a gene amplification reaction, and the detection is amplified gene detection,

[21] an apparatus for analyzing and sorting particles comprising: a flow path cartridge in which a flow path is formed in a transparent substrate, an illumination unit configured to illuminate particles in a sample liquid flowing through the flow path, a detection unit configured to detect particles of interest by detecting scattered light or fluorescence generated from the particles when the particle is illuminated, and identifying the particle based on its signal intensity, wherein the apparatus has a means capable of controlling the gas atmosphere around the sample liquid to a carbon dioxide gas atmosphere of 0.03 to 50%, when the particles are cells

[22] the apparatus for analyzing and sorting particles according to item [21], wherein the control means covers the entire apparatus with a chamber and regulates the carbon dioxide gas atmosphere, and

[23] the apparatus for analyzing and sorting particles according to item [21], wherein the control means regulates carbon dioxide in the gas atmosphere around the liquid in the flow path cartridge.

Advantageous Effects of Invention

In the method for analyzing a specific cell in a high concentration of various cells one by one, a technique of cell sorting, a technique of dispensing a single cell, and a method of analyzing DNA or RNA contained in the cell are important.

According to the apparatus for dispensing particles and the method for dispensing particles of the present invention, it is possible to distinguish between a unmoved luminescent spot that cannot be dispensed, such as scratches and attached foreign matter of the dispensing pipette or a cell that is a particle to be dispensed but adhered to a dispensing pipette, and a movable suspended cell to be dispensed, and thus, it is possible to accurately measure the number of cells that can be dispensed in the dispensing pipette. Therefore, it has become possible to dispense the correct number of cells, in particular a single cell.

According to the apparatus for analyzing particles, the apparatus for sorting particles, and the method for preventing or removing a particles clogged in the flow path of the present invention, in the replaceable micro flow path cartridge, it is possible to automatically execute the method for preventing the flow path being clogged by cells and for removing the clogging after the clogging has occurred, without detaching the micro flow path cartridge from the apparatus.

Further, according to the reaction detector and the method for detecting reaction of the present invention, by using a sensitive gene detection method using emulsion, a plurality of processes including an emulsion formation process, an amplification reaction process of a target gene in the emulsion, and a fluorescence detection process of the emulsion droplet can be carried out in the same flow path of an exchange-type flow path cartridge. This has made it possible to automatically detect target genes sensitively.

BRIEF DESCRIPTION OF THE DRAWINGS

FIGS. 5A-5C is a view (A) showing a process of forming a droplet containing a gene in an emulsion in a micro flow path cartridge, a view (B) showing a gene amplification reaction process after forming a droplet containing a gene in a micro flow path cartridge, and a view (C) showing a process of analyzing the presence or absence of fluorescent of a droplet in an emulsion by flowing back the droplet after a gene amplification reaction in a micro flow path cartridge.

DESCRIPTION OF EMBODIMENTS

[1] Apparatus for Dispensing Particles

The apparatus for dispensing particles of the present invention comprises a transparent hollow pipette for dispensing a sample liquid containing particles, and an image capturing means, and further has means for capturing two or more images of the dispensing liquid in the hollow pipette; means for comparing two or more shot images, distinguishing a moved particle-like substance from an unmoved particle-like substance in the image-captured particle-like substances, and identifying the moved particle-like substance as a suspended particle; and means for dispensing a sample liquid containing a target number of suspended particles.

When dispensing cells, a technique is needed to identify the number of cells in the dispensing pipette. As mentioned above, in techniques for identifying the number of cells, there is a problem in that the scratches, of container or attached foreign matter of the dispensing pipette cannot be distinguished from cells, immediately before dispensing.

The apparatus for dispensing particles of the present invention which solves this issue will be illustrated with reference to the figures.

Figure 3A:
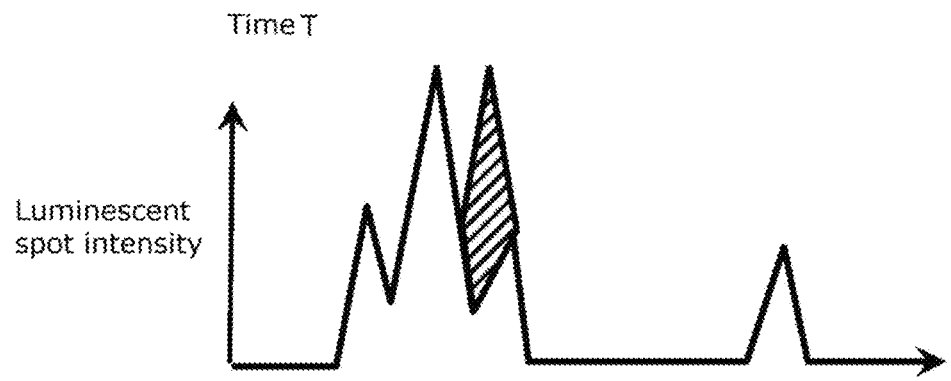
FIGS. 3A-3C is a diagram showing the distribution position (A) of the luminescent spot in the dispensing pipette in direction Z at time T, the distribution position (B) of the luminescent spot in the dispensing pipette in direction Z at time T+ΔT, and the distribution position (C) of the difference between time T and time T+ΔT of the luminescent spot in the dispensing pipette in direction Z.
Figure 3B:
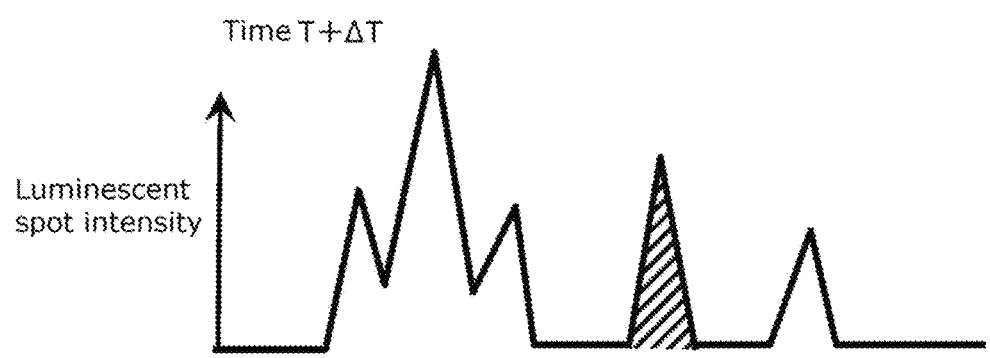
Figure 3C:
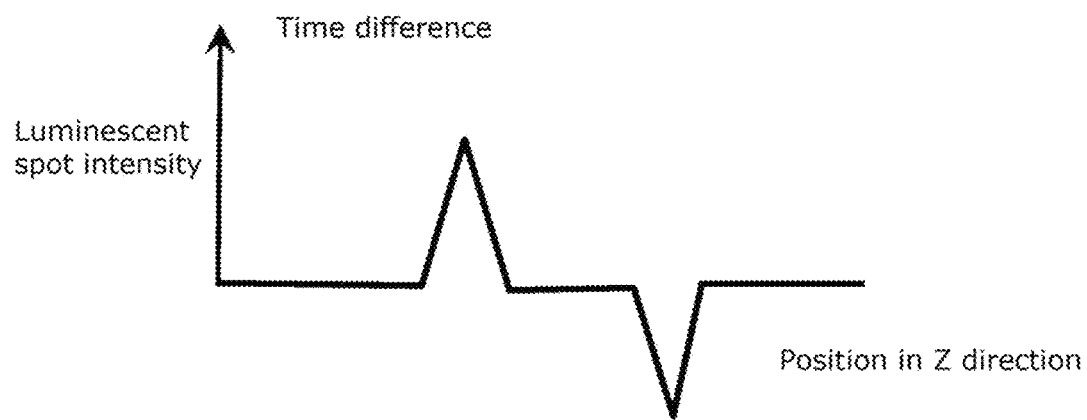

FIG. 3 illustrates a method for distinguishing suspended particles moving within the dispensing pipette from scratches or attached foreign matter of the dispensing pipette. FIG. 3A shows the distribution of the intensity of the luminescent spot spots of the image of the dispensing pipette captured at time T with light illumination with respect to the position in direction Z. FIG. 3B shows the same distribution image-captured at time T+ΔT. FIG. 3C shows the distribution of the difference between time T and time T+ΔT. Only the suspended particles moving with a time difference are detected by the above time difference, by setting the intensity of the luminescent spot due to the scratches and attached foreign matter of the dispensing pipette, which does not change with time difference to become zero. Since the cells move downward by gravity sedimentation, the suspended cells can be detected only by the difference in time.

The hollow pipette and the image capturing means used in the present invention can be used without limitation as the hollow pipette and the image capturing means commonly used in the field.

<<Means for Capturing Two or More Images of the Dispensing Liquid in the Hollow Pipette>>

In the means for capturing two or more images of the dispensing liquid in the hollow pipette, the number of shots and the time interval between shots can be defined. The number of times of shooting is not particularly limited as long as it is two or more times, but is preferably two times. The time interval between shots is not particularly limited as long as the movement of the cells can be detected. For example, it may be taken at a time interval of 0.1 to 60 seconds, and the time interval is preferably 1 to 10 seconds, more preferably 2 to 5 seconds. When the size of cells to be dispensed is 10 the time interval is preferably set so that the movement distance by gravity sedimentation is 20 μm or more.

<<Means for Identifying Suspended Particle>>

In the means for identifying suspended particle of the present invention, the two or more captured images are compared, and the moved particle-like substance is distinguished from unmoved particle-like substances in the image-captured particle-like substances, and the moved particle-like substance is identified as suspended particle.

It is possible to distinguish between the moved particle-like substance and the unmoved particle-like substance by specifying the particle-like substance and determining whether or not the particle-like substance have moved in the second captured image.

<<Dispensing Means>>

The dispensing means used in the present invention may be, without limitation, dispensing means commonly used in this field.

For example, the apparatus for dispensing particles of the present invention is an apparatus for dispensing particles contained in a sample solution one by one. The dispensing pipette is an automatically-replaceable, transparent hollow pipette, and the material thereof is a transparent resin such as polypropylene or polystyrene. The volume of the dispensed liquid is 0.3 µL or less, and the presence and number of particles of 4 µm or more are detected by image recognition of the whole dispensing liquid of the hollow pipette for each dispensing, and then, the particles can be dispensed into the multiwell plate in a specified number. Then, by capturing images of the entire dispensing liquid multiple times at different times, it is possible to distinguish suspended particle moving by gravity sedimentation in the hollow pipette from scratches and attached foreign substances in the hollow pipette and to dispense the suspended particles.

<<Forcibly Moving Means>>

The apparatus for dispensing particles of the present invention may comprise means for forcibly moving the dispensing liquid in the hollow pipette. Although the speed of movement by gravity sedimentation is slow, the suspended particles can be detected quickly by forcibly moving the liquid in the dispensing pipette in a short time. Specifically, forcibly moving means includes a means for changing the air pressure applied to the dispensing liquid in the hollow pipette.

For example, the apparatus for dispensing particles of the present invention is an apparatus for dispensing particles contained in a sample solution one by one. The dispensing nozzle is an automatically-replaceable, transparent hollow pipette, and the volume of the dispensed liquid is 0.3 µL or less. The presence and number of particles of 4 µm or more are detected by image recognition of the whole dispensing liquid of the hollow pipette for each dispense, and then, the particles can be dispensed into the multiwell plate in a specified number. Then, by forcibly moving the liquid in the hollow pipette and capturing a plurality of images of the whole dispensing liquid before and after the movement, it is possible to identify suspended particles in the hollow pipette and to dispense the suspended particles. The volume of liquid forced to move is set between 10 µm and 100 µm. For example, when the size of the cell to be dispensed is 10 µm, it is preferable to move the cell by 20 µm or more. In this case, a pressure fluctuation is set by a displacement of a piston in a cylinder pump.

Figure 14A:
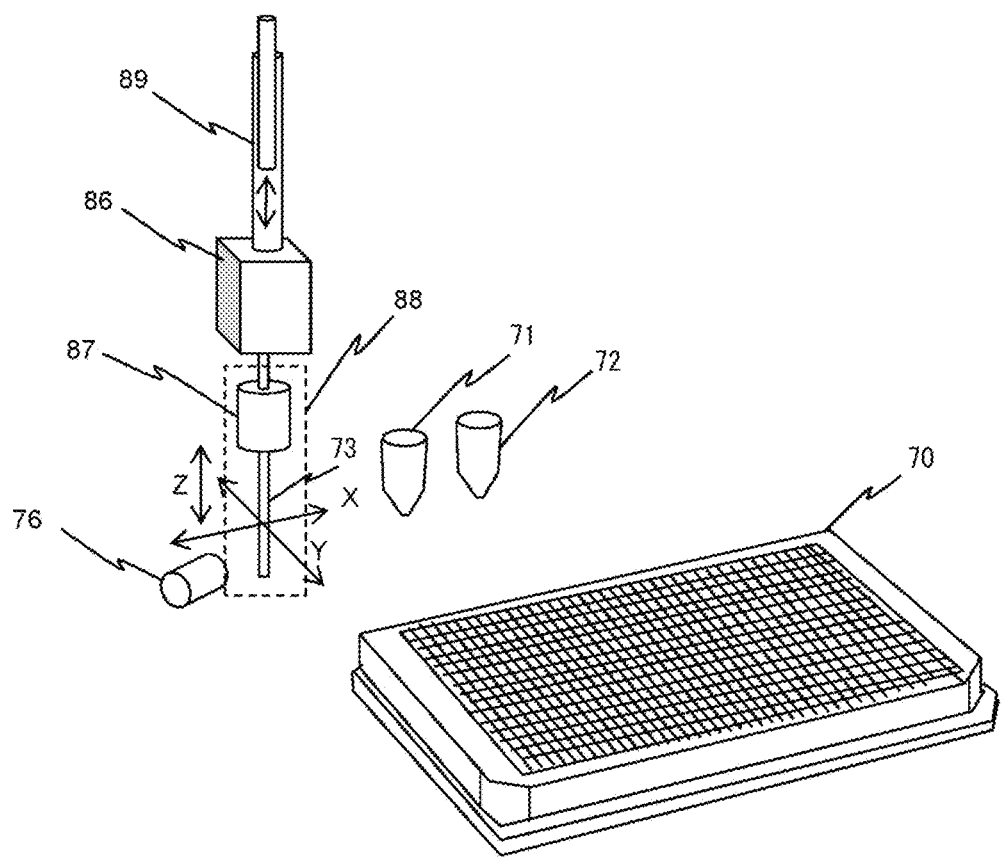
FIG. 14 is a view showing a system for dispensing particles in a sample liquid when the sample liquid is supplied from the upstream of a dispensing pipette, in the apparatus for dispensing particles of the present invention.
Figure 14B:
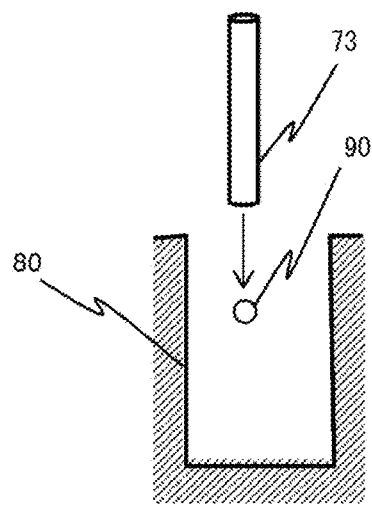
Figure 17:
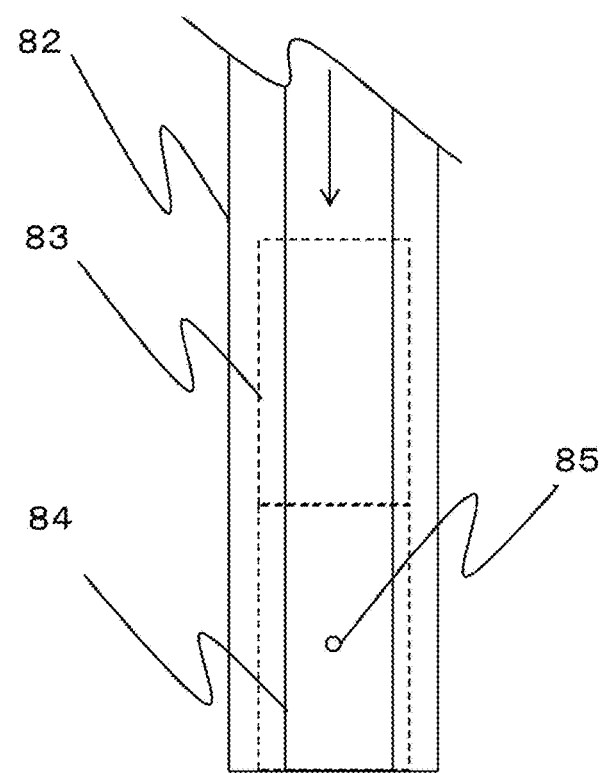
FIG. 17 is a view showing an image recognition method of particles in a sample liquid when a sample liquid is supplied from the upstream of a dispensing pipette in the apparatus for dispensing particles of the present invention.

As a dispensing system, in addition to the case where the sample liquid is drawn up into the dispensing pipette in each dispensing, the sample liquid may be supplied from the top of the pipette. In this case, the aspiration operation is unnecessary in each dispensing, and thus it is possible to continuously supply the liquid. In this case, the part of the sample liquid to be dispensed and the part of the sample liquid to be newly supplied from the upper part are connected continuously, and thus the following improvement is added to the image recognition method based on the difference in time. This improvement will be explained with reference to FIG. 17. The sample liquid is supplied from the upper portion of the dispensing pipette 82 (hollow pipette) for each dispensing. In this case, since the liquid to be dispensed and the liquid to be newly supplied from the upper portion are successive to each other, the boundary between them is unclear. Therefore, there is a problem that the number of cells to be recognized is confused. In order to resolve this problem, two areas, i.e. recognition area 84 and preliminary recognition area 83 in the pipette are set, and particles are detected in each area. The sample liquid is dispensed only when the target number of particles to be dispensed is present in the recognition area and no particles are present in the preliminary recognition area. However, it is possible to eliminate particle contamination by setting the amount of liquid to be dispensed greater than the amount of liquid in the recognition area and less than the total amount of liquid in the recognition area and liquid in the preliminary area, and only the particles included in the recognition area can be dispensed. FIG. 14A shows an example of a dispensing system in which the sample liquid is supplied into the pipette from the upper. The pipetting pipette is movable in the directions X, Y, and Z, and sample liquid 71 is drawn up through the dispensing pipette 73 (hollow pipette)) in advance by the cylinder pump 89 and is stored in the preparatory dispensing chamber 87 at the upper of the dispensing pipette 73. A piezoelectric pump 86 is connected to an upstream side of the preparatory dispensing chamber. As explained in FIG. 17, in the image recognition for particle detection of the image of the inside of dispensing pipette 73 taken by camera 76, the number of particles contained in the area to be dispensed is accurately determined, by setting the recognition area and the preliminary recognition area. When it is determined that the number of particles to be dispensed is within the range of the target set number, as shown in FIG. 14B, each droplet is discharged into the air from the tip of dispensing pipette 73 and dispensed into the multiwell plate by a pulsed pressure of the pump. If the number of particles to be dispensed is not within the range of the target set number, the liquid is returned to sample container 71. In the case of dispensing each droplet, the droplet size ranges from 100 µm to 300 µm. In the system shown in FIG. 14B, the portion within the range indicated by broken line area 88 can be automatically replaceable for each sample liquid, and no carryover between the sample liquids occurs.

The apparatus for dispensing particles for continuously supplying the sample liquid from the upper portion of the hollow pipette has preparatory dispensing chamber 87 for containing the sample liquid for multiple dispensing. The sample liquid can be continuously supplied to the hollow pipette, by having the preparatory dispensing chamber. Further, in order to continuously supply the sample liquid to the hollow pipette from the preparatory dispensing chamber, it is preferable that the apparatus for dispensing particles has a continuous dispensing means. The continuous dispensing means may include, but is not limited to, a piezoelectric pump 86.

Figure 15:
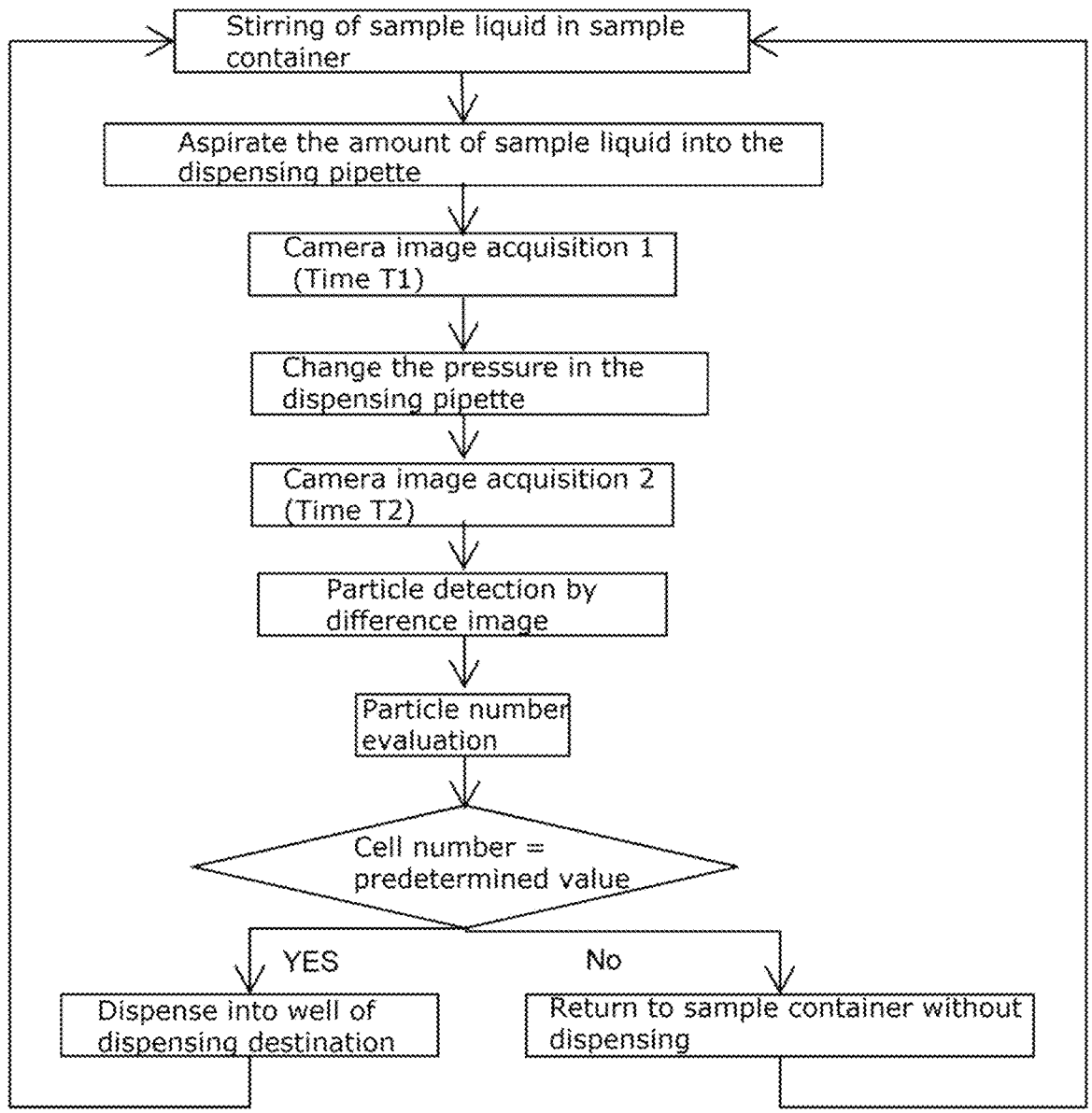
FIG. 15 is a flow chart of a method for aspirating a dispensed liquid into a dispensing pipette for each dispense.
Figure 16:
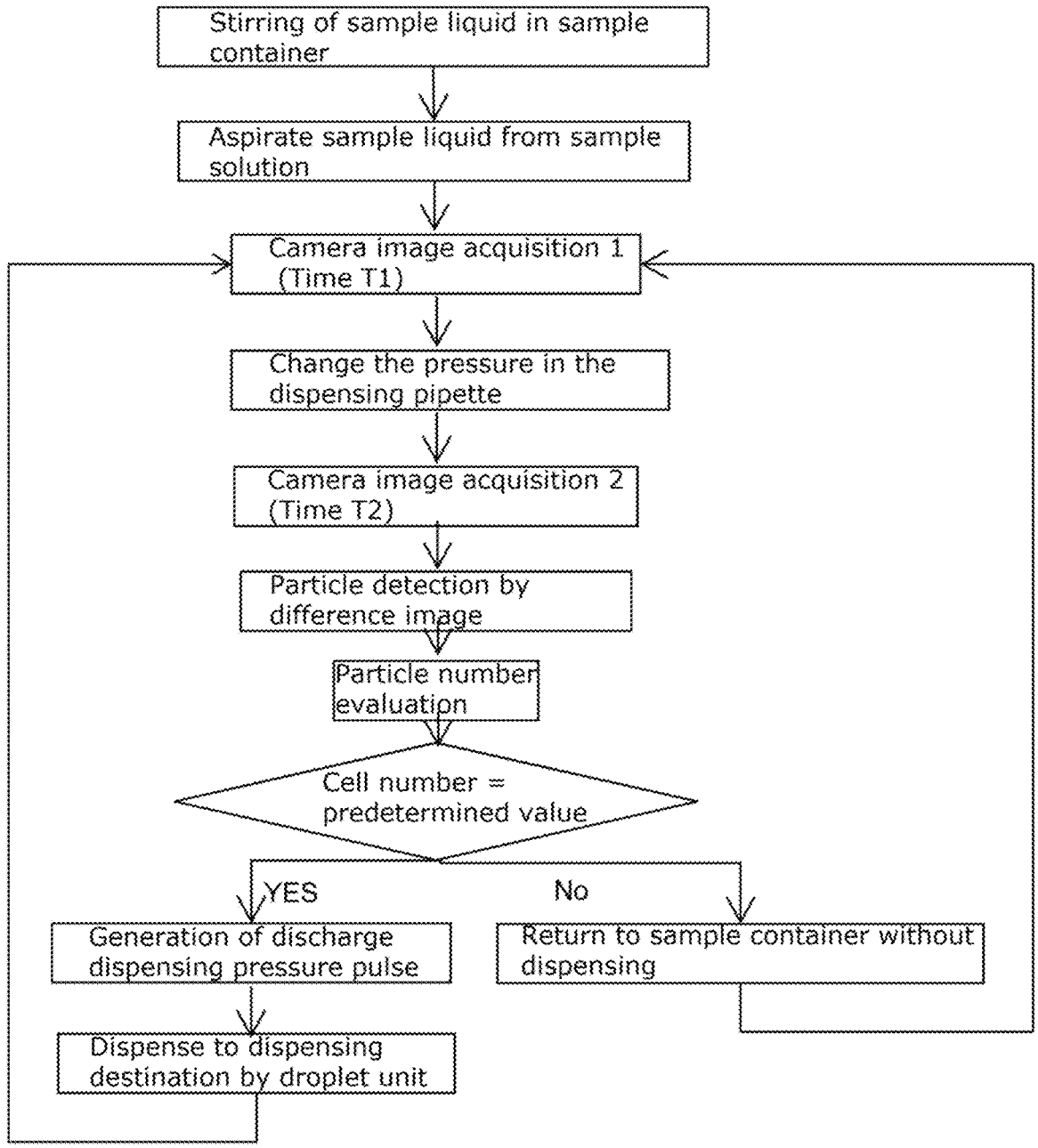
FIG. 16 is a flow chart of a method for continuously dispensing sample liquid from the upper of the dispensing pipette.

FIGS. 15 and 16 are flowcharts showing the respective procedures of the two types of dispensing methods described above. FIG. 15 is a flow chart of the method of aspirating the dispensed liquid into the dispensing pipette for each dispensing. In this case, the particles of the sample liquid in sample container 71 settle out to the bottom due to gravity sedimentation. Therefore, after stirring the sample liquid, it is aspirated by pipetting pipette 73, and thereafter the images in the pipetting pipette are captured multiple times by camera 76. The liquid in the dispensing pipette is forced to move between multiple image acquisitions, by varying the pressure. Suspended particles in the dispensing liquid are detected by comparing multiple images, and when the number of suspended particles satisfies the set value, the liquid is dispensed to the dispensing destination. If not, the liquid is returned to the sample solution without being dispensed. FIG. 16 is a flow chart of a method of continuously supplying sample liquid from the upper of the dispensing pipette. Also in this method, the sample liquid in the sample container is firstly stirred. Instead of aspirating the dispensed liquid for each dispensing, sample liquid volume for the number of dispensing is aspirated at one time in sample liquid preparatory chamber 87 placed upstream of dispensing pipette 73, and then the images in the pipetting pipette are captured multiple times by camera 76. The liquid in the dispensing pipette is forced to move between multiple image acquisitions, by varying the pressure. Suspended particles in the dispensing liquid are detected by comparing multiple images, and when the number of suspended particles satisfies the set value, the liquid is discharged into the air by applying a pulse pressure to sample liquid preparatory chamber 87, to dispense to the dispensing destination. If the number of suspended particles does not satisfy the set value, the liquid is returned to the sample container without being dispensed.

Next, a problem of contamination after dispensing the sample liquid and a technique for preventing the contamination will be explained. For example, there are two sample solutions A and B for dispensing. The cell population contained in sample A is dispensed into a multiwell plate, and subsequently, the cell population contained in sample B is dispensed into another multiwell plate. Considering cell contamination that occurs in this case, the cells of sample A may be contaminated in the multi-well plate into which the cells contained in sample B are dispensed. Techniques to eliminate this risk are described below. In this method, the sample liquid is aspirated and dispensed into the replaceable dispensing pipette for each dispensing, and the dispensing pipette may be replaced after dispensing of sample liquid A. However, when using a flow path in which the dispensing liquid is aspirated from the sample liquid and supplied to the inside of the dispensing pipette from the upstream thereof, It is necessary to replace everything from the flow path for aspirating up the dispensing liquid to the dispensing pipette including the pump. Therefore, it is impossible to prevent contamination only by dispensing pipette replacement. This is because the following possibilities cannot be denied. That is, cells of sample fluid A adhere to the pump, and when sample B is dispensed, the cells separate therefrom and become contaminated. Therefore, the portion in contact with the sample solution needs to be interchangeable. However, if an expensive pump is included in this portion, the running cost of dispensing will be high and it will be impractical. For this reason, in the present invention, even when using a flow path to which the dispensing liquid is supplied from the upstream of the dispensing pipette, the portion in contact with the sample liquid was limited to the part including the sample liquid preparatory chamber 87 and dispensing pipette 73 downstream of the pump, as shown in FIG. 14. Then, by making the portion interchangeable, it is possible to eliminate contamination by exchanging the portion at the time of dispensing the different sample liquid. The sample preparatory chamber is initially installed to draw up a sample volume that does not require drawing up the sample liquid for each dispensing and to store the sample solution upstream of the dispensing pipette.

<<Carbon Dioxide Control Means>>

In order to eliminate cell damage in the cell dispensing, the method of dispensing in the same gas atmosphere as a $CO_2$ incubator may be mentioned.

Figure 13:
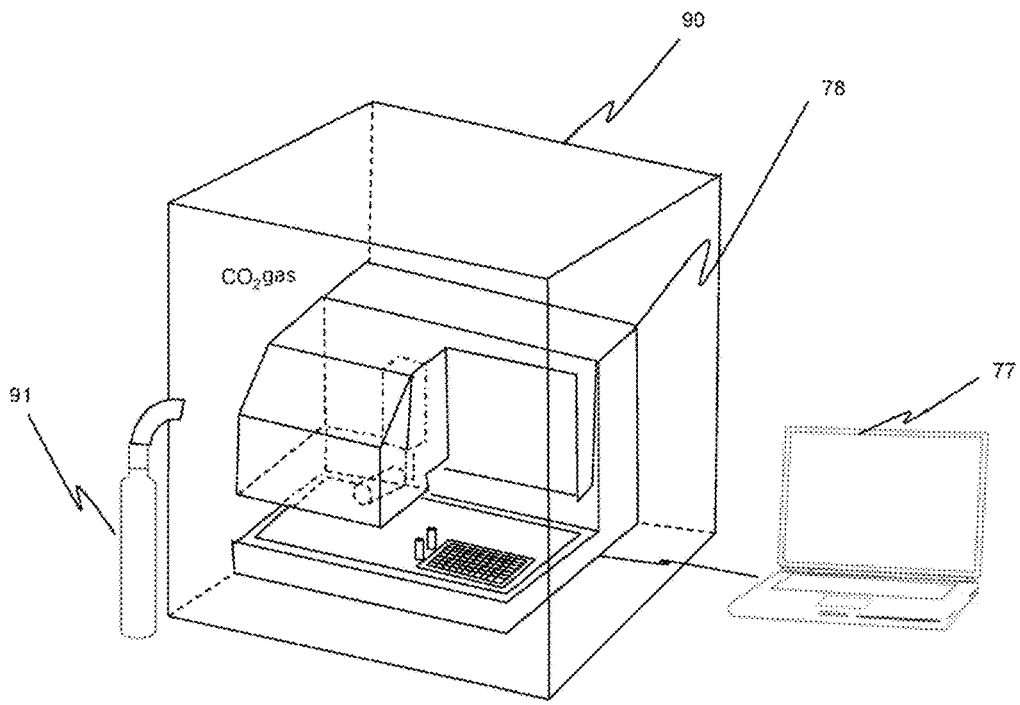
FIG. 13 is a view showing an exemplary method for dispensing in a 5% $CO_2$ gas atmosphere in the apparatus for dispensing particles of the present invention.

That is, the apparatus for dispensing particles of the present invention may have means for controlling the gas atmosphere to a carbon dioxide gas atmosphere of 0.03 to 50%. The controlling means is not particularly limited as long as the carbon dioxide concentration can be 0.03% or more, which is the carbon dioxide concentration in the atmosphere. The carbon dioxide concentration used in the particle dispensing method described later is not particularly limited, but is preferably 2 to 10% by volume, more preferably 3 to 7% by volume, more preferably 4 to 6% by volume, and most preferably 5% by volume. FIG. 13 is a view showing an exemplary method for dispensing cells in an atmosphere in which the carbon dioxide gas concentration is adjusted. In this figure, the dispensing apparatus is surrounded by a container that maintains an atmosphere in which the carbon dioxide gas concentration is adjusted.

Figure 18:
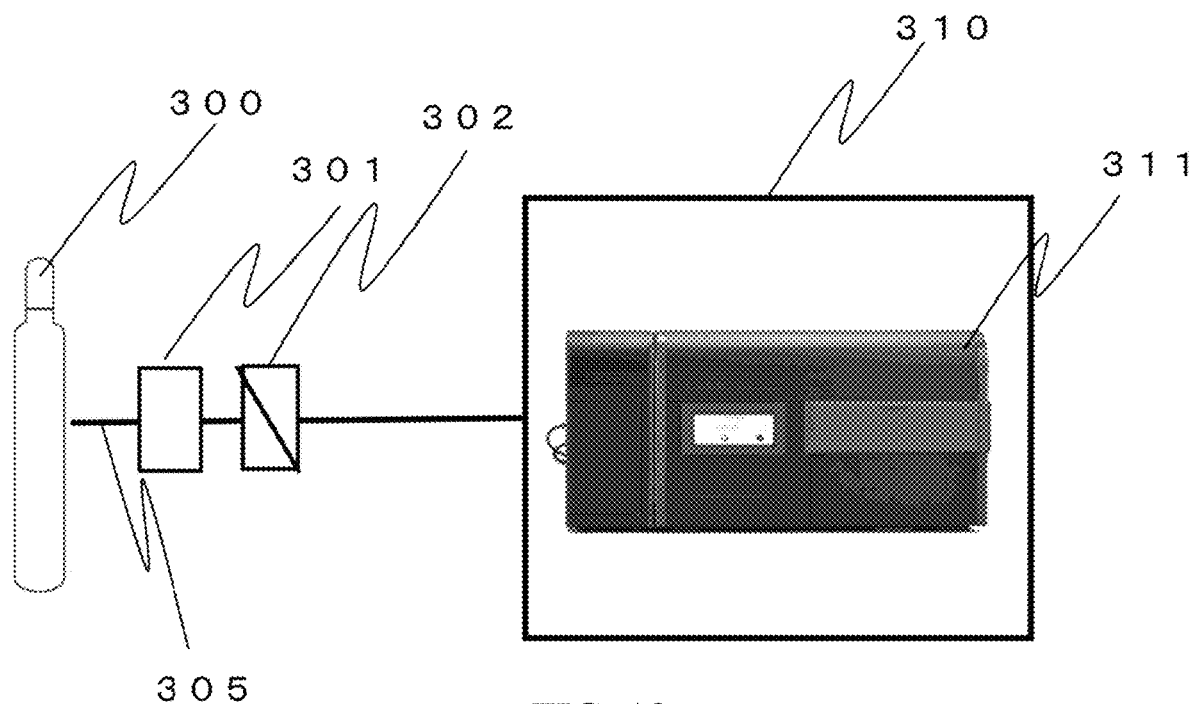
FIG. 18 is a view showing a method for performing cell sorting in a $CO_2$ atmosphere by installing a cell sorter in a $CO_2$ chamber. This approach achieves cell sorting in $CO_2$ without relying on cell sorting principles.

For example, the apparatus for dispensing particles of the present invention is an apparatus for dispensing particles contained in a sample solution one by one. The dispensing nozzle is an automatically-replaceable, transparent hollow pipette, and the volume of the dispensed liquid is 0.3 μL or less. The presence and number of particles of 4 μm or more are detected by image recognition of the whole dispensing liquid of the hollow pipette for each dispensing and then, the particles can be dispensed into the multiwell plate in a specified number. During the dispensing process, the gas atmosphere in the apparatus can be maintained at 5% carbon dioxide gas. Here, the suspended cells moving by natural sedimentation in the hollow pipette may be detected separately from scratches or attached particles of the hollow pipette by capturing images of the entire dispensed liquid a plurality of times at different periods of time. Further, the suspended cells moving in the hollow pipette may be detected separately from scratches or attached particles of the hollow pipette by forcibly moving the liquid in the hollow pipette and acquiring a plurality of images of the whole dispensing liquid before and after the movement. Dispensing of cells is often intended to dispense some of the cells of interest contained in the various cell populations. In this case, it is preferable to subject the dispensing cells to pretreatment using a cell sorter, in order to purify the target cells from the various cell populations. The cell sorting process is also performed in an atmosphere in which the carbon dioxide concentration is adjusted in the same manner as the cell dispensing process, whereby cell damage caused by exposure to the atmosphere can be reduced as in cell dispensing. That is, it is preferable to analyze or separate the cells, in order to prevent deterioration of bioavailability of the cells. For example, in the case of performing cell sorting as shown in FIG. 18, the cell sorter may be installed and operated in a container in an atmosphere in which the carbon dioxide concentration is adjusted. A container with an atmosphere in which the carbon dioxide concentration is adjusted, is air tightly connected by a $CO_2$ gas cylinder (300), a pressure regulator (301) and an air pipe (303), and the inside thereof contains carbon dioxide gas, and the pressure is almost atmospheric pressure. The cell sorter may be a device utilizing a micro flow path cartridge, and may be a cell sorter capable of separating cells drop by drop in the atmosphere, which is generally called FACS. In the devices utilizing micro flow path cartridge, the sample liquid is present in a reservoir in the micro flow path, and thus, its volume is in the range of 10 μL to several tens of mL. Therefore, the volume of gas around the sample liquid is also in that range. That is, a small volume is suitable to control the atmosphere to a constant $CO_2$ gas concentration.

Figure 19:
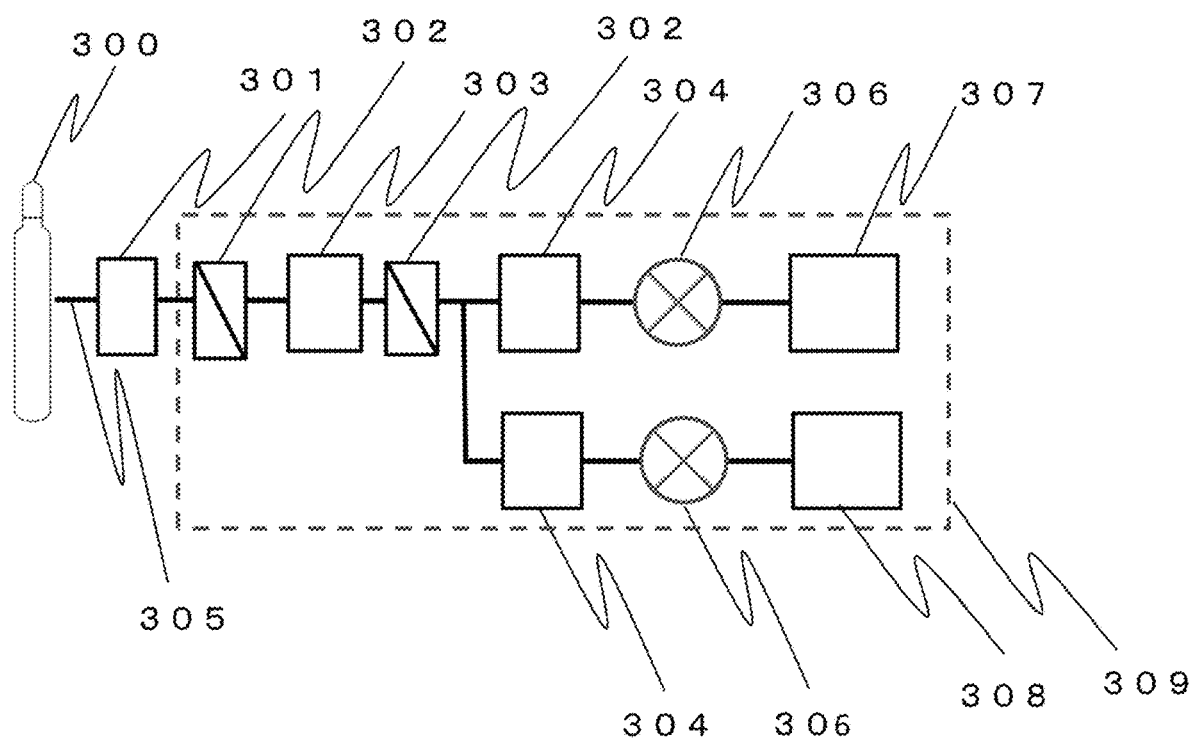
FIG. 19 is a view showing a method for realizing cell sorting in a $CO_2$ atmosphere by making the inside of reservoirs of the interchangeable micro flow path cartridge shown in FIG. 2 into a $CO_2$ atmosphere.

Furthermore, FIG. 2 shows the cell sorter that controls the flow of liquid in the micro flow path cartridge by pneumatic control. In this cell sorter, a means for sending $CO_2$ gas to the sample reservoir for storing the sample liquid and the collection reservoir for storing the target sorted cells in the cartridge is shown in FIG. 19. In this case, the $CO_2$ gas cylinder (300), the pressure regulator (301), and the air pipe (305) are air tightly connected to the $CO_2$ gas pipe system of the cell sorter device. The $CO_2$ pipe system in the apparatus is air tightly connected to the sample reservoir (corresponding to 11 in FIG. 2) in the micro flow path cartridge and the collection reservoir (corresponding to 17 in FIG. 2) in the micro flow path cartridge via a peristaltic pump (304). In pneumatic controls in different reservoirs, $CO_2$ pipe system is connected parallelly to the reservoirs by different peristaltic pumps because of the different times at which the $CO_2$ gases are delivered. The advantages of using the perister pump are as follows. Since the amount of inflowing gas and the amount of exhausting gas are always constant, the control system of the gentle inflow and exhaust of $CO_2$ gas does not affect the pressure regulation of the pneumatic control for controlling the flow of cells in the airtight reservoir

[2] Method for Dispensing Particles

The method for dispensing particles of the present invention uses a device for dispensing particles comprising a transparent hollow pipette for dispensing sample liquid containing particles, and an image capturing means, to dispense particles, and comprises the steps of: (1) capturing two or more images of a dispensing liquid in the hollow pipette, (2) comparing two or more shot images, and distinguishing a moved particle-like substance from an unmoved particle-like substance in the image-captured particle-like substances, to identify the moved particle-like substance as a suspended particle; and (3) dispensing a sample liquid containing a target number of suspended particles. The method for dispensing particles of the present invention is not limited, but can be conducted using the apparatus for dispensing particles of the present invention. Specifically, the dispensing may be carried out according to the method described in item of the above "[1] apparatus for dispensing particles".

[3] Apparatus for Analyzing Particles and Apparatus for Sorting Particles

The apparatus for analyzing particles of the present invention comprises a flow path cartridge in which a flow path is formed in a transparent substrate, an illumination unit configured to illuminate particles in a sample liquid flowing through the flow path, and a detection unit configured to detect particles of interest by detecting scattered light or fluorescence generated from the particles when the particle is illuminated, and identifying the particle based on its signal intensity. In the apparatus for analyzing particles, a sample reservoir connected to a first flow path; a sheath reservoir to which a second flow path and a third flow path joined from the left and right sides of the first flow path are connected; and a discharged liquid reservoir connected to a downstream side of the first flow path after joining; are formed on the cartridge. The apparatus for analyzing particles has a means for flowing back a sheath fluid in the sheath reservoir to the sample reservoir by making the pressure in the sheath reservoir higher than the pressure in the sample reservoir.

The apparatus for sorting particles of the present invention comprises a flow path cartridge in which a flow path is formed in a transparent substrate, an illumination unit configured to illuminate particles in a sample liquid flowing through the flow path, a detection unit configured to detect particles of interest by detecting scattered light or fluorescence generated from the particles when the particle is illuminated, and identifying the particle based on its signal intensity, and a force generating unit configured to apply a force for changing a flow direction to the particles based on the signal from the detection unit. In the apparatus for analyzing particles, a sample reservoir connected to a first flow path; a sheath reservoir to which a second flow path and a third flow path joined from the left and right sides of the first flow path are connected; and a discharged liquid reservoir connected to a downstream side of the first flow path after joining; are formed on the cartridge. The apparatus for analyzing particles has a means for flowing back a sheath fluid in the sheath reservoir to the sample reservoir by making the pressure in the sheath reservoir higher than the pressure in the sample reservoir.

In the apparatus for sorting particles, the flow path cartridge may has a fourth branched flow path and a fifth branched flow path which are oppositely connected to both sides of the first flow path in which the second flow path and the third flow path are joined; and a sorting reservoir connected to the fourth branched flow path and a collection reservoir connected to fifth branched flow path. Further, the force generating unit may generate a pulse flow flowing in the direction from the fourth branched flow path to the fifth branched flow path so as to sort the particles into the collection reservoir by changing the flow of particles in the direction of the fifth branch flow path.

The means for making the pressure in the sheath reservoir higher than the pressure in the sample reservoir includes a means for applying pressure to the sheath reservoir (such as a pump), a means for applying pressure to the sample reservoir (such as a pump), and individual means (pumps) instead of one means (pump). It can be achieved by using these means.

Further, the apparatus for analyzing particles or the apparatus for sorting particles of the present invention, preferably has a means (for example, a pump) for applying pressure to a discharged liquid reservoir, a sorting reservoir, and/or a collection reservoir. Preferably, the means (pump) is different from the means (pump) for applying pressure to the sheath reservoir.

[4] Method for Preventing or Removing Flow Path Clogging

In the method for preventing or removing a clog in the flow path of the present invention, the apparatus for analyzing particles or the apparatus for sorting particles is used.

That is, in the apparatus for analyzing particles or the apparatus for sorting particles, the pressure in the sheath reservoir is made higher than the pressure in the sample reservoir, and the sheath fluid in the sheath reservoir flows back to the sample reservoir, to prevent or remove the particles clogged in the flow path from the sample reservoir.

As mentioned above, the pressure in the sheath reservoir is increased using a separate means (pumps) as the means for applying pressure to the sheath reservoir (such as a pump) and the means for applying pressure to the sample reservoir (such as a pump), and whereby the sheath fluid in the sheath reservoir can be flowed back to the sample reservoir, which can prevent or remove the clogging by particles in the flow path.

The pressure applied to the sheath reservoir is not particularly limited as long as it is higher than the pressure applied to the sample reservoir, but is preferably 2 kPa to 50 kPa, more preferably 5 kPa to 20 kPa. The pressure applied to the sample reservoir is also not particularly limited, but is preferably −2 kPa to 1 kPa, more preferably −1 kPa to 0 kPa.

The difference between the pressure applied to the sheath reservoir and the pressure applied to the sample reservoir is also not particularly limited, but is preferably 4 kPa to 50 kPa, and more preferably 7 kPa to 20 kPa.

Further, the pressure applied to the discharged liquid reservoir, the sorting reservoir, and/or the collection reservoir is also not particularly limited, but is preferably −1 kPa to 0 kPa, more preferably −0.5 kPa to 0 kPa.

The time for maintaining the pressure in the sheath reservoir higher than the pressure in the sample reservoir is not particularly limited as long as the clogging by particles in the flow path can be prevented or removed. For example, it is 1 second to 1 minute, preferably 1 to 10 seconds, more preferably 2 to 5 seconds, and even more preferably 2 to 4 seconds. In addition, the interval for changing the pressure for this stirring is preferably a fixed time interval to prevent the flow path clogging. The following cases may be mentioned as timing for detecting a sign of the flow path clogging and generating a change in pressure for stirring: the number of detected particles per unit time (detection rate) in the state of flowing particles falls below a set threshold, or the detection rate falls below a set relative decrease rate. For the purpose of both prevention of flow path clogging and removal of flow path clogging, it is desirable to generate stirring pressure change when any of the above conditions are satisfied.

Figure 1A:
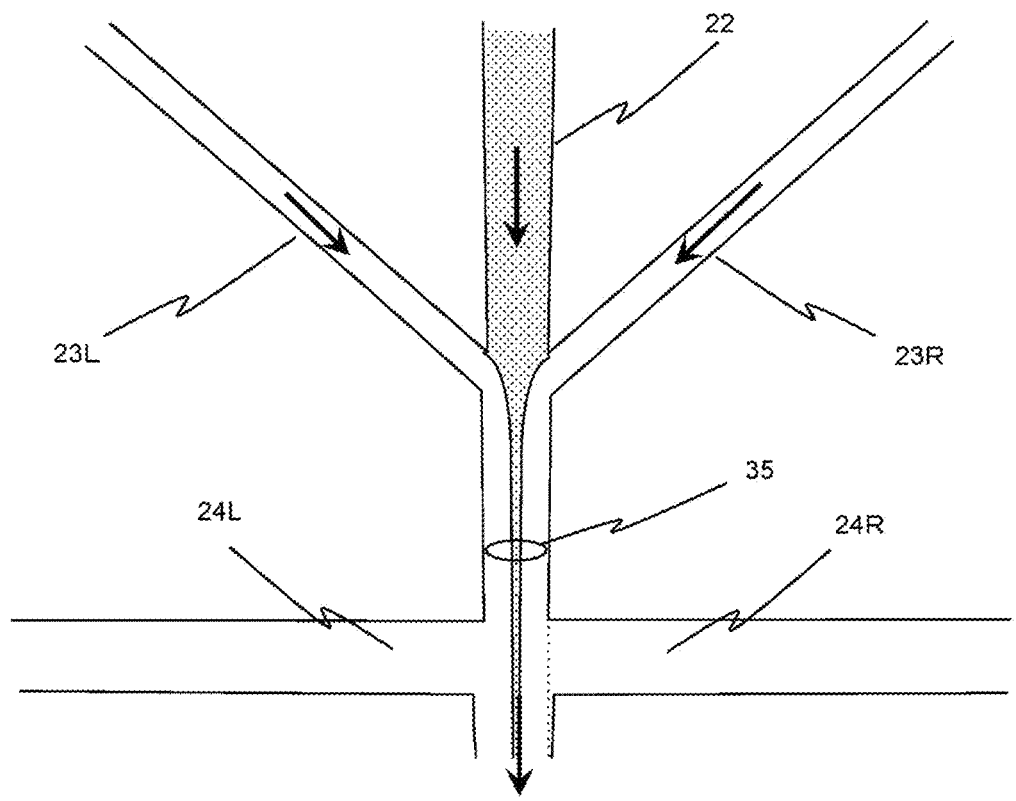
FIGS. 1A-1B is a view (A) showing the state of the normal flow of liquid in an interchangeable flow path cartridge for cell sorting, and a view (B) showing the flow of sheath liquid to prevent or remove the cell clogged in the interchangeable flow path cartridge for cell sorting.
Figure 1B:
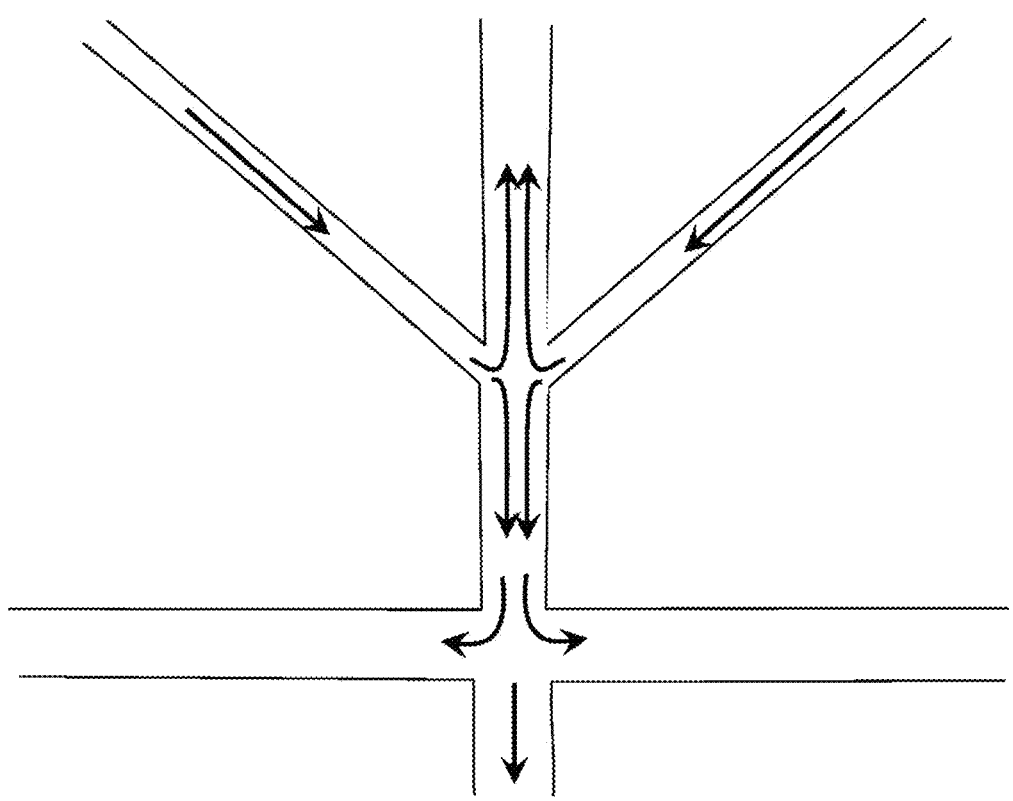
Figure 2A:
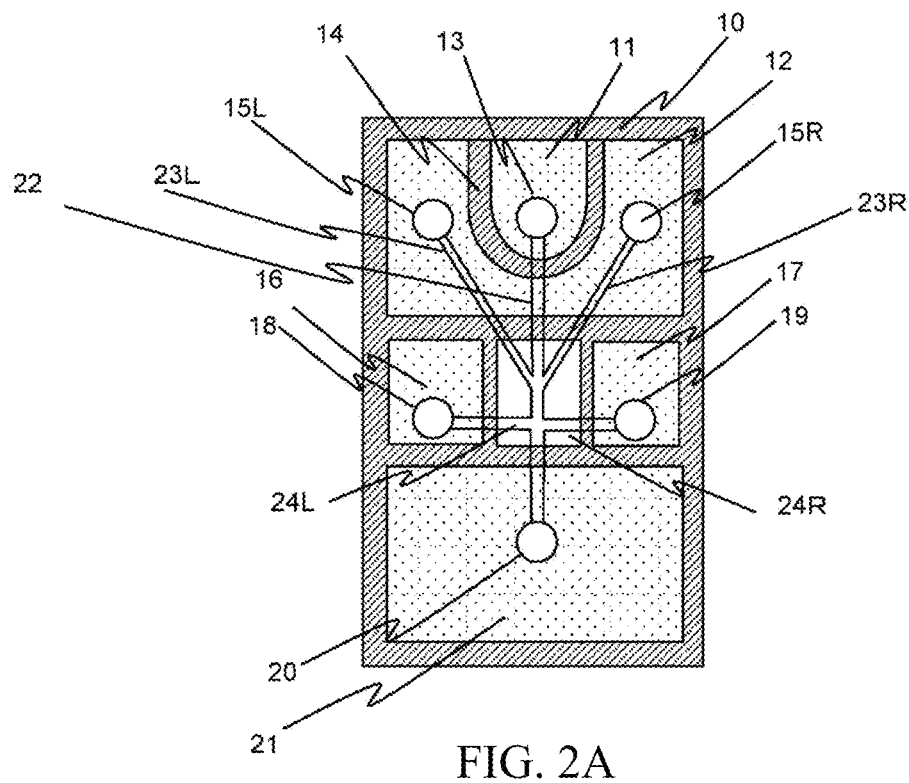
FIGS. 2A-2B is a plan view (A) of an interchangeable flow path cartridge for cell sorting, and a view (B) showing cells being deposited by gravity sedimentation at the bottom of the sample reservoir of the interchangeable flow path cartridge for cell sorting, being stirred by causing the sheath solution to flow back to the sample reservoir.
Figure 2B:
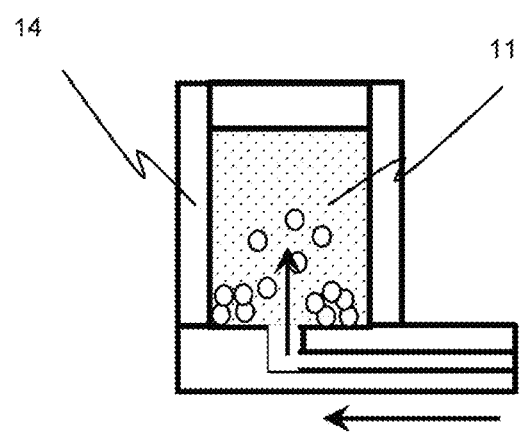

One embodiment of the stirring means for preventing or removing the particles clogged in the flow path is explained using FIGS. 1 and 2. FIG. 1(A) shows a flow path pattern of the interchangeable micro flow path cartridge for sorting, and FIG. 2 (A) shows a plan view of the cartridge. The sorting method using this cartridge is the method for sorting target cells by pulsed air pressure described in the above Patent literature 6. The sample liquid containing cell flows in flow path 22 connected to the sample reservoir 11. Flow path 23L and flow path 23R in which sheath fluid containing no cells flows join in this flow path from the left and right so that the sample liquid converges on and flows in the center of the flow path. When cells pass through laser illumination region 35, scattered light or fluorescence generated from the cells are detected to determine whether or not they are the target cells or not. When it is determined that the cell is a target cell, a pulse flow is generated to flow from flow path 24L to flow path 24R when the cell passes through the intersection area of flow path 24L and flow path 24R, which is sorting area. As a result, the target cells are sorted to flow path 24R, and the non-target cells pass through and flow into the discharged liquid reservoir. The above is the flow of the liquid at the time of sorting. When this state is continued, cells are deposited with time by gravity sedimentation at the bottom of sample reservoir 11. Therefore, cells often clog in the connection port portion of sample reservoir 11 and flow path 22. Thus, the pressure applied to sample reservoir 11 and the pressure applied to sheath reservoir 12 are temporarily changed. As shown in FIG. 1(B), air pressure is applied only to the sheath reservoir to flow the sheath fluid in flow path 23L and flow path 23R, and the air pressure applied to sample reservoir 11 is made zero. As a result, the sheath fluid flows back to sample reservoir 11, and the cells deposited on the bottom of the sample reservoir are stirred with the sheath fluid. In FIG. 2B, it is schematically illustrated that the cells deposited at the bottom of sample reservoir 11 are stirred by the backflow of the sheath flow. When the pressure applied to sheath reservoir 12 is increased, the backflow is increased and thus the stirring force is increased. In addition, the cells taken up by sorting do not flow out to the discharged liquid reservoir by the stirring Therefore, cell stirring can be achieved by only temporarily changing the pressure applied to each reservoir in the sorting process.

One embodiment of the stirring means of the apparatus for analyzing particles will be explained below. That is, the stirring means in the flow path without sorting function is explained. For example, the apparatus for analyzing particles comprises a flow path cartridge in which a flow path is formed in a transparent substrate; an illumination unit configured to illuminate particles in a sample liquid flowing through the flow path; and a detection unit configured to detect particles of interest by detecting scattered light or fluorescence generated from the particles when the particle is illuminated, and identifying the particle based on its signal intensity, and analyzes the particles flowing through the flow path of the cartridge based on a signal from the detection unit. The apparatus for analyzing particles uses a flow-path chip in which a reservoir for sample liquid connected to the first flow path (sample reservoir), and a reservoir connected to the second and third flow paths joining from the left and right sides of the first flow path (sheath reservoir), and a fourth reservoir connected to a downstream side of the first flow path after joining (waste fluid reservoir) are formed. In the apparatus for analyzing particles, while flowing samples for cell analysis processing, the pressure of each reservoir is temporarily changed only for a predetermined time. That is, the pressure applied to the sample liquid in the sample reservoir is changed from the setting value A for analysis processing (positive pressure) to zero. On the other hand, the pressure applied to the sheath fluid in the sheath fluid reservoir is increased from the setting value B for analysis processing (positive pressure). Further, the pressure applied to the waste fluid in the discharged liquid reservoir is changed from the setting value C for analysis processing (negative pressure) to zero. The temporary change in pressure stops the outflow of cells from the sample reservoir to the outside, and causes backflow of sheath fluid from the reservoir bottom to which the flow path of the sample reservoir is connected. As a result, cells deposited by gravity sedimentation at the bottom of the sample reservoir are stirred.

One embodiment of the stirring means of the apparatus for sorting particles will be explained below. For example, the apparatus for sorting particles comprises a flow path cartridge in which a flow path is formed in a transparent substrate, an illumination unit configured to illuminate particles in a sample liquid flowing through the flow path, a detection unit configured to detect particles of interest by detecting scattered light or fluorescence generated from the particles when the particle is illuminated, and identifying the particle based on its signal intensity, and a force generating unit configured to apply a force for changing a flow direction to the particles flowing through the flow path of the cartridge based on the signal from the detection unit. The flow path cartridge comprises a reservoir for sample liquid connected to the first flow path (sample reservoir), and a reservoir connected to the second and third flow paths joining from the left and right sides of the first flow path (sheath reservoir), and a fourth branched flow path and a fifth branched flow path are oppositely connected to both sides of the first flow path after joining. Further, a third A reservoir for delivering a pulse flow, which is connected to the fourth branched flow path (sorting reservoir), a third B reservoir for sorting and collecting particles by changing the flow of the particles in the direction of the fifth branched flow path, using the pulse flow flowing from the fourth branched flow path to the fifth branched flow path generated by the force generation means, which is connected to the fifth branched flow path (collection reservoir), and a fourth reservoir for storing unsorted particle, which is connected downstream of the first flow path (discharged liquid reservoir), are formed thereon. Then, while flowing samples for sorting processing, the pressure of each reservoir is temporarily changed only for a predetermined time. That is, the pressure applied to the sample liquid in the sample reservoir is changed from the setting value A for sorting processing (positive pressure) to zero. On the other hand, the pressure applied to the sheath fluid in the sheath fluid reservoir is increased from the setting value B for sorting processing (positive pressure). Further, regarding the pressure applied to the waste fluid in the discharged liquid reservoir, the sheath fluid may flow to the collection reservoir. Due to the temporary pressure change, cell-free sheath fluid flows temporarily from the sheath reservoir to the sample reservoir, the sorting reservoir, the collection reservoir, and the discharged liquid reservoir. In the process, the flow of cells in the sample reservoir is stopped, and the cells deposited by gravity sedimentation in the bottom of the sample reservoir are stirred by back flowing the sheath liquid to the bottom of the sample reservoir to which the flow path is connected. In addition, the sheath fluid flows into the collection reservoir, and therefore, the cells collected by sorting in the collection reservoir are prevented from flowing out to the discharged liquid reservoir. As described above, stirring of cells in the flow path chip can be performed without affecting sorting performance.

[5] Reaction Detector

The reaction detector of the present invention is for reacting sample liquid in micro flow path cartridge and detecting the result of the reaction, and comprises a sample reservoir, a reagent reservoir, an oil reservoir, and a droplet reservoir, and wherein a first flow path from the sample reservoir and a second flow path from the reagent reservoir join to form a third flow path, a fourth flow path and a fifth flow path from the oil reservoir join the third flow path from both sides thereof, the third flow path is connected to the droplet reservoir downstream of the junction of the fourth flow path and the fifth flow path, the reaction detector has a means for flowing back droplets in the droplet reservoir through the third flow path, and has a means for detecting the reaction in the third flow path.

In the reaction detector of the present invention, a mixed solution in which the sample and the reagent are preliminarily mixed may be used. In this case, the sample reservoir and the reagent reservoir may be one sample reagent reservoir, and the first flow path and the second flow path may be one third flow path from the sample reagent reservoir.

<<Reaction of Sample Liquid>>

The reaction of sample in the reaction detector of the present invention is not particularly limited, and the reaction generally used in the field can be used without limitation. For example, there may be mentioned a gene amplification reaction, a protein phosphorylation reaction, and a GPCR and peptide binding reaction. As the gene amplification reaction, there may be mentioned a PCR method such as digital PCR, a LAMP method, or a SmartAmp method.

<<Detection of Reaction>>

The method for detecting reaction in the reaction detector of the present invention can be appropriately selected according to the type of reaction. For example, when the reaction product exhibits a feature such as fluorescence, luminescence, or color development, a detection method according to the feature can be used. Specifically, there may be mentioned a means for detecting fluorescence emitted by light irradiation with a light source such as a laser or an LED, or a means for detecting chemiluminescence.

<<Means of Adjusting Temperature of Droplet Reservoir>>

The reaction detector of the present invention preferably has means of adjusting the temperature of the droplet reservoir. Reactions of various analytes can be conducted by means of adjusting the temperature of the droplet reservoir. The means of adjusting the temperature is not particularly limited, but a means capable of raising temperature (heating), lowering temperature (cooling), and maintaining temperature is preferable. Increase in temperature (heating), decrease in temperature (cooling), and maintenance of temperature can be performed by means commonly used in this field.

<<Means for Flowing Back the Droplets>>

The Means for flowing back the droplets in the reaction detector of the present invention is not particularly limited as long as the droplets can be flowed back to the flow path from the droplet reservoir. There may be mentioned a means for making the pressure applied to the droplet reservoir higher than the pressure applied to the sample reservoir, reagent reservoir, and oil reservoir. In particular, when back flowing the droplet only to a specific upstream reservoir, there is an advantage that the emulsion after fluorescence detection can be recovered from one reservoir. The diagnosis is completed by the detection of ctDNA in blood. However, if the gene sequence is to be further confirmed, it is necessary to recover the droplets having fluorescence, and therefore, there is a merit to backflow the droplets into one reservoir.

If droplets are back flowed only to the sample reservoir, positive pressure may be applied to the droplet reservoir, negative pressure may be applied to the sample reservoir, positive pressure may be applied to the oil reservoir, and positive pressure may be applied to the reagent reservoir.

The purpose is achieved by using the means for applying pressure to the sheath reservoir (for example, syringe pump, or combination of positive pressure rotary pump and electro-pneumatic regulator, combination of negative pressure rotary pump and electro-pneumatic regulator), the means for applying pressure to the sample reservoir and the like (for example, syringe pump, or combination of rotary pump and electro-pneumatic regulator), and the means for adjusting the pressure individually applied (for example, syringe pump, or combination of positive pressure rotary pump and electro-pneumatic regulator, combination of negative pressure rotary pump and electro-pneumatic regulator) as the specific means for making the pressure applied to the droplet reservoir higher than the pressure applied to the sample reservoir and the like. As the means for adjusting the pressure individually applied, in the case of the syringe pump, both positive pressure and negative pressure can be handled depending on the piston movement direction, and in the case of the electro-pneumatic regulator connected to the rotary pump, both positive pressure and negative pressure can be handled by connecting the electro-pneumatic regulator connected to the positive pressure rotary pump and the electro-pneumatic regulator connected to the negative pressure rotary pump are connected parallelly.

Most preferably, means for applying pressure to the droplet reservoir (pump), means for applying pressure to the reagent reservoir (pump), means for applying pressure to the oil reservoir (pump), and applying pressure to the droplet reservoir (pump) are each individual means (pump).

[6] Method for Detecting Reaction

The method for detecting reaction of the present invention uses the reaction detector. That is, the method for detecting reaction of the present invention comprises (1) forming a droplet in oil by supplying oil to a mixture of sample and reagent from both sides of the third flow path through the fourth flow path and the fifth flow path, (2) reacting the sample in the droplet, and (3) detecting the reaction of the sample in the droplet.

In the method for detecting reaction of the present invention, a mixed solution in which the sample and the reagent are preliminarily mixed, can be used. In this case, the sample reservoir and the reagent reservoir may be one sample reagent reservoir, and the first flow path and the second flow path may be one third flow path from the sample reagent reservoir. Therefore, the method for detecting reaction can be performed by adding the mixture to the sample reagent reservoir.

<<Droplet Forming Step>>

In the droplet forming step of the method for detecting reaction of the present invention, the droplet is formed by supplying oil to a mixture of sample and reagent from both sides of the third flow path through the fourth flow path and the fifth flow path.

Droplets suitable for the reaction can be formed, by appropriately adjusting the flow rate of the mixture and the flow rate of the oil. It is possible to form droplets, for example, by flowing at 1 to 100 volume, preferably 2 to 50 volume, more preferably 3 to 10 volume of oil to 1 volume of the mixed solution.

The oil is not particularly limited as long as it can form droplets, but includes a mineral oil, fluorine oil such as Fluorinert, silicone oil, or the like.

<<Sample Reaction Step>>

The reaction in the sample reaction step is not particularly limited, and commonly used reactions in this field can be used without limitation. For example, there may be mentioned a gene amplification reaction, a protein phosphorylation reaction, and a GPCR and peptide binding reaction. As the gene amplification reaction, there may be mentioned a PCR method such as digital PCR, a LAMP method, or a SmartAmp method. In the case of the PCR method, increase in temperature (heating), decrease in temperature (cooling), and maintenance of temperature are performed. That is, gene amplification reaction can be performed, by alternately maintaining a high temperature (such as 95° C.) and a moderate temperature (such as 65° C.) for predetermined times. In the case of isothermal amplification method such as LAMP method or SmartAmp method, gene amplification reaction can be performed, for example, by maintaining the temperature at 65° C.

<<Reaction Detection Step>>

The detection method in the reaction detection step can be appropriately selected according to the type of reaction. For example, when the reaction product exhibits a feature such as fluorescence, luminescence, or color development, a detection method according to the feature can be used. Specifically, there may be mentioned a means for detecting fluorescence emitted by light irradiation with a light source such as a laser or an LED, or a means for detecting chemiluminescence.

It is preferable to flow back the droplets from the droplet reservoir to the third flow path, and to detect the reaction in the third flow path.

Figure 4A:
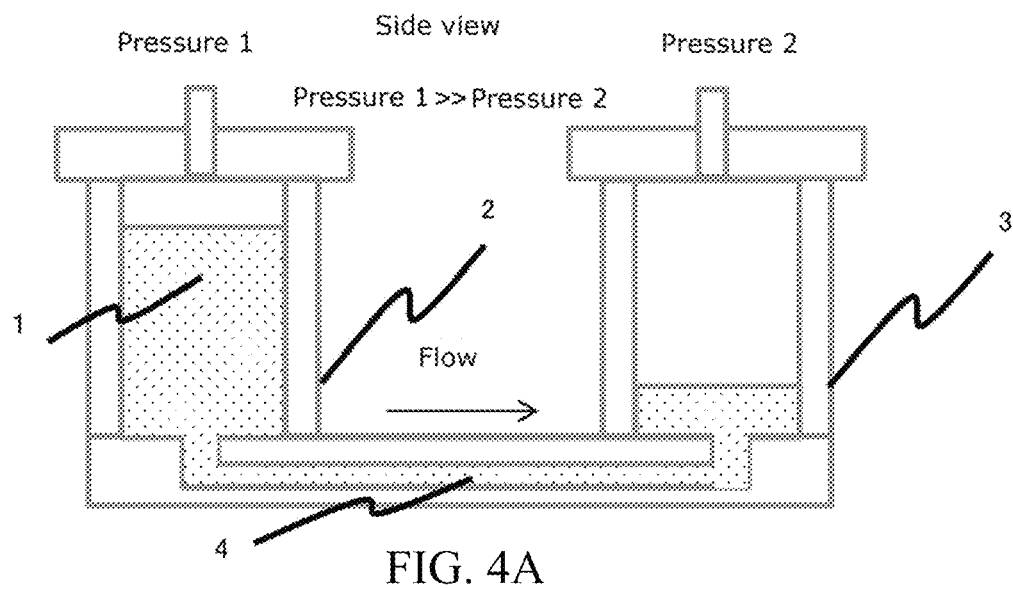
FIGS. 4A-4C is a view (A) showing a process in which the sample liquid in the upstream reservoir of the interchangeable flow path cartridge flows by pressure control through the flow path connected to the downstream reservoir, a view (B) showing a quiescent state of the sample liquid after all the sample fluid in the upstream reservoir of the interchangeable flow path cartridge has flowed to the downstream reservoir, and a view (C) showing a process in which the quiescent state of sample liquid in the downstream reservoir of the interchangeable flow path cartridge flows back by reversing the pressure.
Figure 4B:
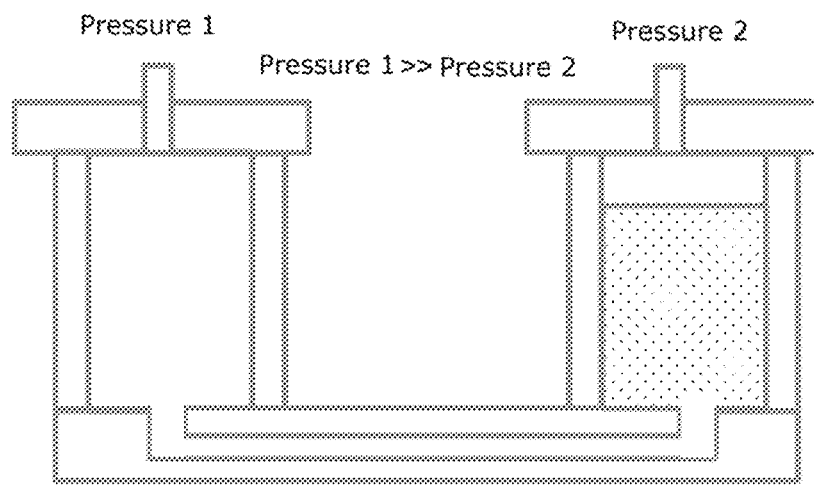
Figure 4C:
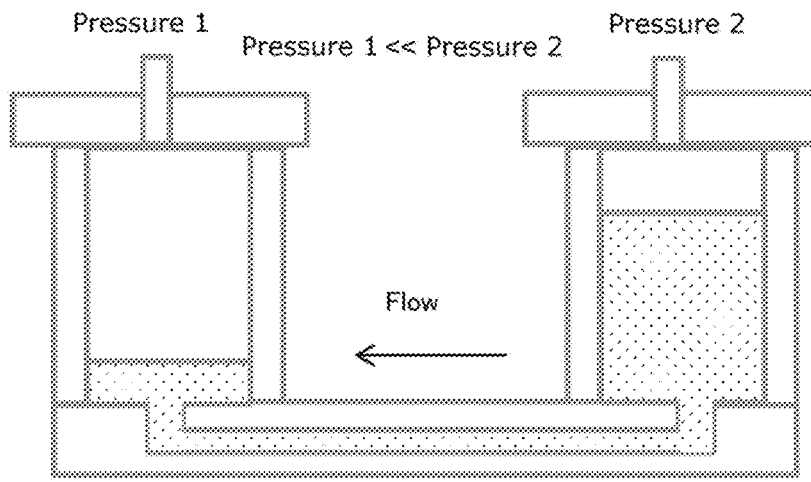

The mechanism of processing in the reaction detector and method for detecting reaction of the present invention will be explained below. In the disposable, interchangeable type micro flow path cartridge, different reactions and/or detections are sequentially performed while flowing the sample liquid. To that end, one embodiment of the method for performing multiple processes with different processing times with the same flow path cartridge will be explained using FIG. 4. In FIG. 4, the most upstream reservoir 2 and the most downstream reservoir 3 formed in the disposable interchangeable micro flow path cartridge are connected by flow path 4. First, process 1 for moving the sample liquid 1 in reservoir 2 to reservoir 3 is conducted, by controlling pressure 1 applied to the upper surface of the sample liquid in reservoir 2 and pressure 2 applied to reservoir 3. By moving all the sample liquid to reservoir 3, process 1 is completed, and the flow automatically stops and becomes stationary. This process is referred to as process 2. Next, a back flow is made from reservoir 3 to reservoir 2. This process is referred to as process 3. As described above, different processes 1, 2 and 3 including flow and stationary can be sequentially executed only with control of pressure 1 and pressure 2.

One specific embodiment of the reaction detector and the method for detecting reaction will be explained below. In this embodiment, a plurality of processes are sequentially executed in the same flow path using backflow by pneumatic control, and this method can be applied to a method for detecting genes with high sensitivity using droplets in an emulsion. In this embodiment, the three processes of droplet formation process, gene amplification reaction, and detection are conducted in the same micro flow path cartridge. When three types of processing ((1) droplet formation, (2) gene amplification, (3) detection) which require different times are sequentially performed, the flow of droplets is stopped during the reaction time in the process of gene amplification. Therefore, a mechanism for stopping the flow of droplets, such as a valve, is required in the flow path. In the present invention, the gene amplification reaction is performed by the droplet reservoir so as not to use the mechanism, and that is, the flow of droplets is naturally stopped. Then, after completion of the reaction, the droplets are back flowed and detected. In such control, it is not necessary to use a special element in the replaceable micro flow path. That is, That is, the control can be performed only by switching the air pressure, and thus the running cost is low and the cost performance is high. FIG. 5(A) is a plan view of the flow path cartridge, showing a flow path pattern for forming droplets containing a gene in an emulsion. The sample liquid containing DNA or RNA of cells, bacteria, virus or the like, is applied to sample reservoir 102-1 and an aqueous solution containing the reagents necessary for gene amplification reaction is applied to reagent reservoir 102-2. Oil for forming an emulsion of droplets in oil is applied to oil reservoir 102-3. A mineral oil or fluorine oil such as Fluorinert can be selected as this oil. In this state, an air pressure greater than atmospheric pressure is applied to sample reservoir 102-1, reagent reservoir 102-2, and oil reservoir 102-3, and an air pressure less than the atmospheric pressure or the air pressure upstream is applied to droplet reservoir 103-1, so as to generate the flow. Then, the flow paths respectively connecting sample reservoir 102-1 and reagent reservoir 102-2 are joined and mixed, and then the oil flows of oil reservoir 102-3 are joined from the left and right. As a result, droplets in oil are formed, and the droplets flow into droplet reservoir 103-1. The above is the droplets formation process in emulsion. In the droplets formation process in emulsion, it is desirable that a sufficient number of droplets be formed until the sample liquid is finished. In FIG. 5 (B), the applied pressure holds the same pressure as that shown in FIG. 5 (A) or a low pressure that does not cause backflow, so that the droplets population in oil flowing into droplet reservoir 103-1 remains in droplet reservoir 103-1 In this state, the reaction for amplifying the target gene sequence contained in the droplet is performed. As gene amplification reaction, a method utilizing isothermal amplification and a method utilizing PCR can be conducted. When using PCR, the temperature of the droplet reservoir 103-1 is alternately changed between about 95° C. and about 65° C. for a predetermined interval and predetermined number of times. In the case of the isothermal amplification method, amplification reaction is conducted at 65° C., and two methods, i.e. Lamp method and SmartAmp method are known. In any method, a sufficient amplification reaction is carried out by maintaining the temperature of droplet reservoir 103-1 at a temperature of about 65° C. for at least about 30 minutes or more. The droplets in emulsion containing the amplified gene emit fluorescence in proportion to the amount of gene by using a fluorescent probe. After the gene amplification reaction, droplets in the emulsion are detected. This process is shown in FIG. 5(C). Droplets in the emulsion flow back from droplet reservoir 103-1, by making the pressure applied to droplet reservoir 103-1 greater than the pressure applied to sample reservoir 102-1, reagent reservoir 102-2, and oil reservoir 102-3. Then, the droplet having fluorescence is detected by irradiating the flow path with laser 106. As described above, the three processes of emulsion formation, gene amplification and detection can be processed in the same cartridge.

EXAMPLES

The present invention now will be further illustrated by, but is by no means limited to, the following Examples.

Example 1

Figure 9A:
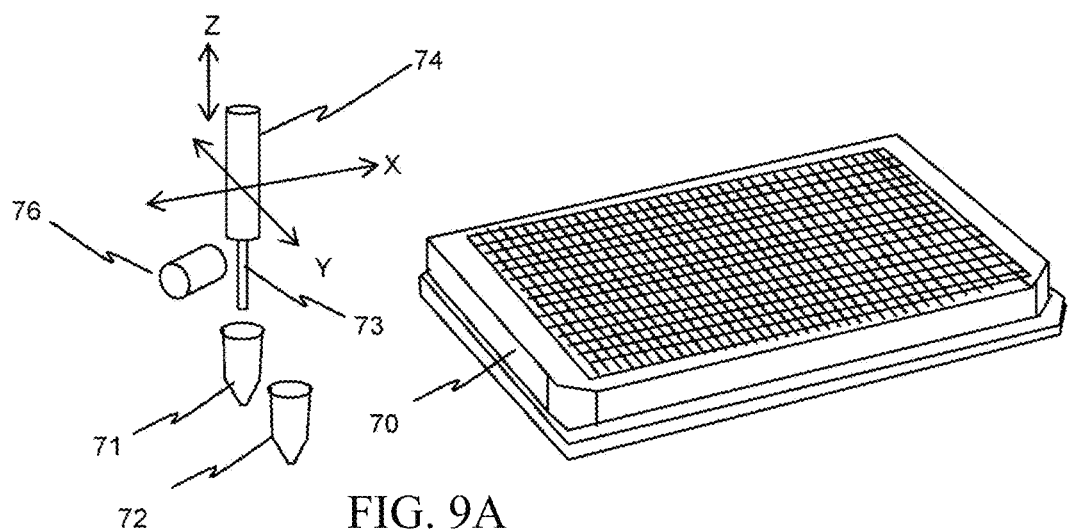
FIGS. 9A-9C is a view (A) showing a dispensing head portion of the apparatus for dispensing particles of the present invention, a view (B) showing the operation of the dispensing head of the apparatus for dispensing particles, and a view (C) showing the overview of the apparatus for dispensing particles.
Figure 9B:
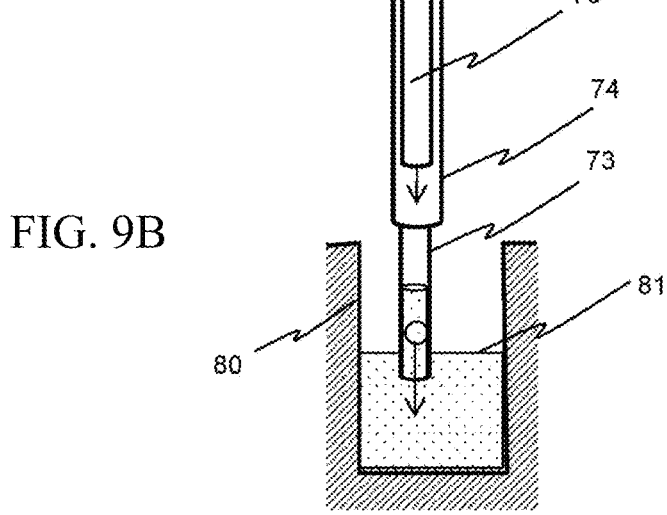
Figure 9C:
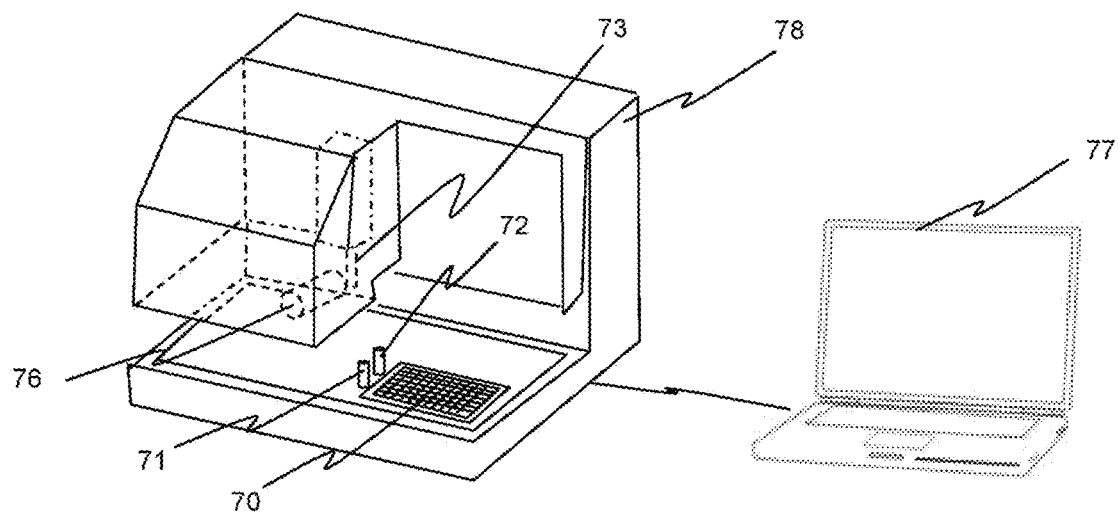
Figure 10A:
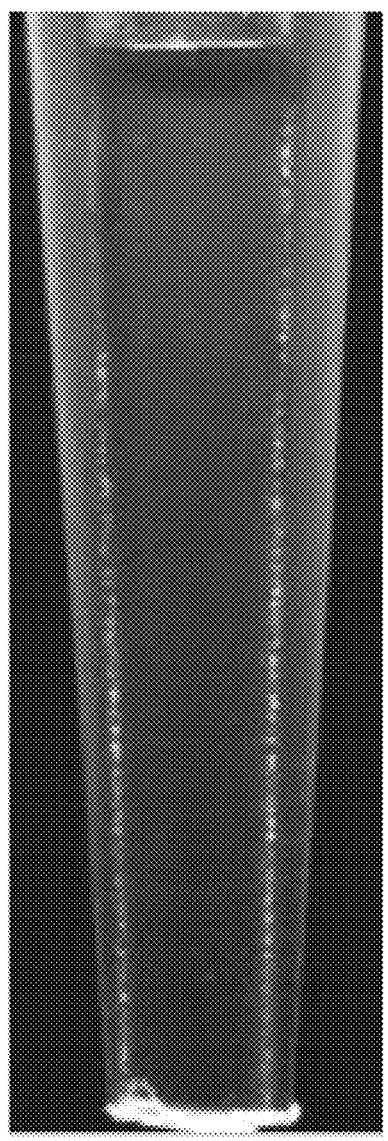
FIGS. 10A-10C is an image (A) of the sample liquid in the dispensing pipette, a time difference image (B) of the sample liquid in the dispensing pipette, and an enlarged view (C) of the portion where the settling particle was recognized, in the apparatus for dispensing particles of the present invention.
Figure 10B:
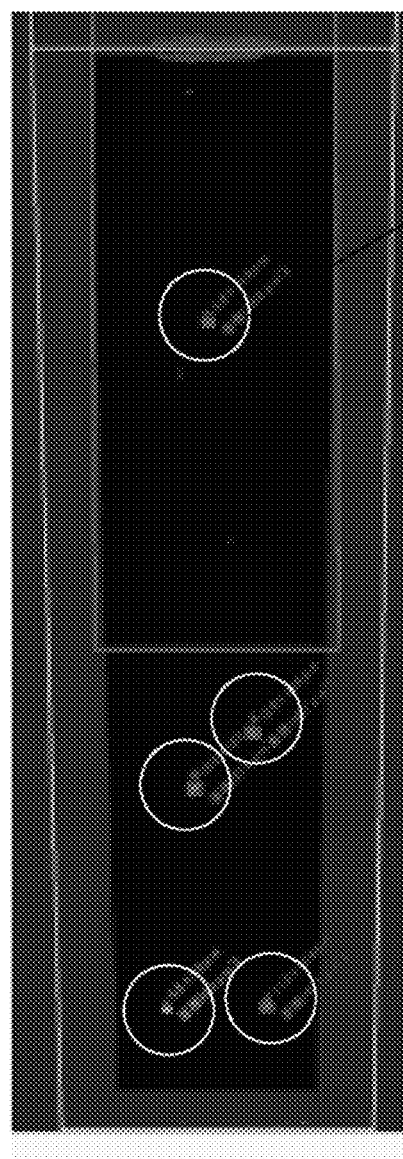
Figure 10C:
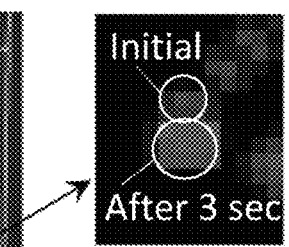

In this example, the method for dispensing particles was carried out using the apparatus for dispensing particles of the present invention. Specifically, cells were dispensed one by one into a multi-well plate. The apparatus for dispensing cells is schematically shown in FIG. 9 (A). The cell suspension before dispensing is applied in tube 71. The cells settle by gravity to the bottom of tube 71, and thus, it is necessary to stir the cells at time intervals of at least 5 minutes. If the time interval for stirring increases, the area without cells in the upper layer of the cell suspension expands, so it is necessary to strictly maintain the time interval. A transparent hollow pipe attached below syringe pump 74 that controls air pressure, i.e., the tip of dispensing pipette 73, is inserted into the cell suspension by downward movement on the Z-axis. Next, the piston of the syringe is drawn up by the amount to be dispensed, and the cell suspension is aspirated into pipette 73. After aspiration, pipette 73 is drawn upward in the Z-axis, and an image of the entire dispensing volume in the pipette is captured twice by the camera. In this case, when the time difference of image capture is 3 seconds, the movement distance by weight sedimentation of cells having a size of about 10 μm is 10 μm or more. Therefore, the suspended cells can be distinguished from scratches or attached foreign matter in the dispensing pipette by time difference. FIG. 10 shows an example of detecting the number of the suspended cells in a dispensing pipette containing cells by image recognition of time difference. FIG. 10 (A) is the first captured image, FIG. 10 (B) is the captured image of the time difference, and FIG. 10 (C) is an enlarged partial image of the cells detected by the time difference image. In FIG. 10 (A), there are many luminescent spots such as scratches or attached foreign matters of the dispensing pipette. Luminescent spots changed in 3 seconds are found in FIG. 10(B), and specifically, the number of suspended cells is recognized as 5. The luminescent spots of the cells before and after the time difference of 3 seconds is shown in FIG. 10 (C). The images of these two luminescent spots correspond to the two parts i.e. the plus and minus part of the luminance distribution of the time difference in FIG. 3(C). The above embodiment is a cell detection method by the time difference before and after movement by gravity sedimentation of cells. When the liquid in the dispensing pipette is forced to move vertically by pressure, the speed of movement can be faster than that by gravity sedimentation, so the time interval of the time difference can be shortened. Then, the number of cells in the dispensing pipette is analyzed by time difference image detection. If one cell exists therein, the dispensing pipette is moved to the well of the specified address of the multiwell plate. Dispensing pipette 73 is moved downward in the Z-axis, and as shown in FIG. 9B, it is lowered below upper surface 81 of the liquid which is already dispensed. Piston 75 of the syringe pump is pushed to discharge the droplets in the pipette. After discharging, the dispensing pipette is drawn up while pushing down piston 75. Image recognition in the dispensing pipette is performed, and if the number of droplets is zero or two or more, dispensing pipette 73 is returned to tube 71 and the emulsion in dispensing pipette 73 is discharged. Then, the emulsion is aspirated again and dispensed only when there is only one droplet. When the internal diameter of the pipette is 400 μm and the dispensing volume is 0.3 μL, it is sufficient to aspirate 2.4 mm into the pipette. Next, it is considered whether it is possible to shoot an entire 0.3 μL liquid volume with a single shot image of the camera in focus. When using an objective lens of 1×, the depth of field is 440 μm, and thus the entire pipette with an inner diameter of 400 μm can be imaged in focus. Considering the size of the field of view, the ½ inch camera has a field of view of 6.4 mm. and therefore, it is possible to capture the entire pipette with a length of 2.4 mm. Accordingly, it is possible to image the entire 0.3 μL dispensing volume in one captured image. In addition, the resolution of the image is 11 μm, and thus the presence or absence of single cell and the number of cells can be identified. The optical system is described below. The light source that illuminates the cells in the dispensing pipette is the LED, and it illuminates downward from the upper of the dispensing pipette. In the detection optical system, cells with a particle diameter of 10 μm contained in a hollow pipette with an inner diameter of 400 μm which is made of transparent resin are image-captured with a 1× objective lens and a ½ inch camera, and the depth of field is 400 μm or more. FIG. 9 (C) shows an overview of the dispenser. The dispenser can be placed in a safety cabinet by size. Cell damage can be reduced by covering and using the dispenser with a container with a 5% $CO_2$ gas atmosphere.

Example 2

In this example, the method for preventing or removing particles clogged in the flow path was conducted using the apparatus for sorting particles of the present invention.

Specifically, using the interchangeable micro flow path cartridge for cell sorting shown in FIG. 2(A), the cells clogged in the flow path was prevented or removed by stirring. The material of the substrate of the flow path cartridge is a transparent resin and is any of COP, COC, and PMMA. The main flow path 22 has a width of 80 μm and a depth of 80 μm. When sorting is performed, a pressure of 1.8 kPa is applied to sample reservoir 11, a pressure of 1.8 kPa is applied to sheath reservoir 12, and a pressure of −0.8 kPa is applied to discharged liquid reservoir 21. When the electromagnetic valve is closed, no pressure is applied to reservoirs 16 and 17 related to sorting. Regarding the pressure in the case of stirring, the pressure applied to sample reservoir 11 is 0 kPa, the pressure applied to sheath reservoir 12 is 7 kPa, and the pressure applied to the discharged liquid reservoir 21 is 0 kPa. In order to examine the stirring effect when the above pressures were maintained for only 3 seconds, a PBS suspension of a high concentration of cultured cells (Molt 4 cell) at $10^8$ cells/mL was placed in the sample reservoir. Then, a pressure of 1.8 kPa was applied to sample reservoir 11, a pressure of 1.8 kPa was applied to sheath reservoir 12, and a pressure of −0.8 kPa was applied to discharged liquid reservoir 21, and sorting was performed. A laser with a wavelength of 488 nm was illuminated to flow path 22 to count the number of flowing cells. About 6 minutes after the start of measurement, the number of cells decreases and becomes zero. This is because the flow path is clogged by the cells settling and depositing at the bottom of the sample reservoir. At this time, when the pressure for stirring is applied for 3 seconds, the number of cells increases from zero. That is, it can be seen that clogged cells are removed. Furthermore, it can be seen that the number of cells increases even if the pressure for stirring is applied before the number of cells reaches zero. The above data shows that the stirring in the present invention is effective. In order to automatically carry out the stirring during sorting, 1) the stirring is automatically conducted at predetermined time interval, or
2) the stirring is automatically conducted, when the counting rate goes below a predetermined value. That is, by stirring when any of a plurality of conditions is satisfied, it is possible to cope with both prevention of cell clogging and elimination after cell clogging.

Example 3

Figure 11:
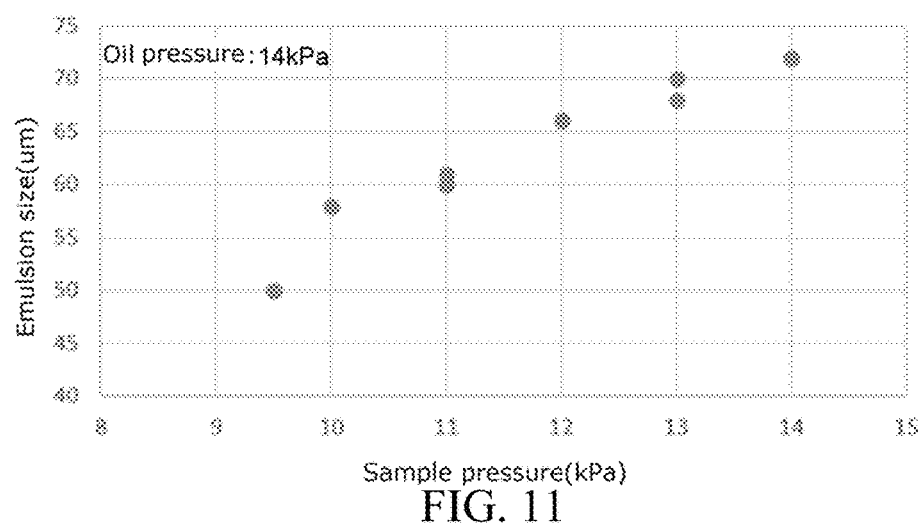
FIG. 11 is a graph showing the relationship between the pressure conditions for droplet formation in emulsion and droplet size.

In this example, the method for detecting reaction was conducted using the reaction detector of the present invention. Specifically, multiple processes in an interchangeable micro flow path cartridge were processed automatically. That is, the three steps of droplet formation in emulsion, gene amplification reaction, and detection were performed in one micro flow path cartridge. FIG. 5 (A) is a plan view of the flow path cartridge, and shows a flow path pattern for forming a droplet containing a gene. A sample liquid containing DNA is placed in sample reservoir 102-1, and a reagent necessary for gene amplification reaction by isothermal amplification and a fluorescent reagent that emits fluorescence upon binding to DNA are placed in reagent reservoir 102-2. For such a fluorescent reagent, 488 nm laser and 637 nm laser are used as illumination light sources. In this case, Evergreen or Cybergreen, which is intercalator type, or TaqMan probe such as FAM or Cy5 is used as a fluorescent dye for gene detection can be used. The oil reservoir 102-3 contains oil for forming droplets in the oil. A mineral oil or fluorine oil such as Fluorinert can be selected as this oil. The emulsion formation conditions are as follows. The pressure applied to oil reservoir 102-3 is 14 kPa, and the pressure applied to sample reservoir 102-1 and reagent reservoir 102-2 is 10 kPa. Droplet reservoir 103-1 is under atmospheric pressure. When using mineral oil containing multiple surfactants (Span 80, Tween 80, Triton X-100) as the oil under this pressure condition, an emulsion droplet of about 55 μm in size is formed as shown in FIG. 11. The width of the flow path forming the emulsion is 40 The formed emulsion flows into droplet reservoir 103-1. The above-mentioned process is the droplet forming step. In the droplets formation in the emulsion, it is desirable that a sufficient number of droplets be formed until the sample liquid is exhausted. As shown in FIG. 5(B), the droplets in the oil that has flowed into droplet reservoir 103-1 accumulate in droplet reservoir 103-1. Then, by maintaining the same pressure as in FIG. 5(A), maintaining the temperature of the droplet reservoir 103-1 at 65° C., and allowing it to stand for at least 30 minutes, the target gene sequence contained in the emulsion droplets is amplified.

Figure 12A:
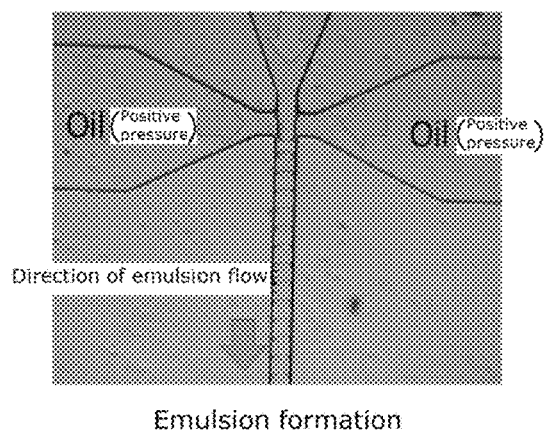
FIGS. 12A-12B is a photograph (A) of the micro flow path in the droplet formation process and a photograph (B) of the back flow of the emulsion containing droplets from the droplet reservoir.
Figure 12B:
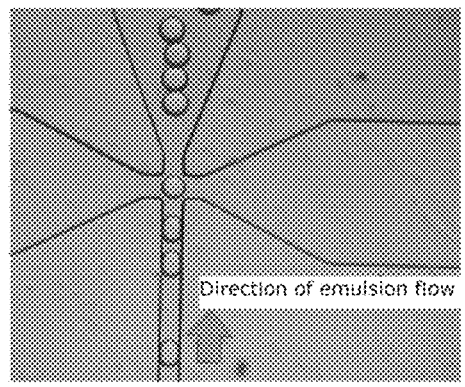

In the gene amplification reaction, droplets in the emulsion are counted. This process is shown in FIG. 5(C). A pressure of 14 kPa is applied to droplet reservoir 103-1, and the pressure applied to sample reservoir 102-1, reagent reservoir 102-2, and oil reservoir 102-3 is set to 0 kPa, which is the atmospheric pressure. According to this pressure condition, the emulsion containing droplets flows back from the droplet reservoir 103-1. FIG. 12(A) is a photograph showing that the emulsion is formed in the micro flow path, and FIG. 12(B) is a photograph showing that the emulsion containing droplets is back flowed from droplet reservoir 103-1. The droplets having fluorescence are detected by illuminating the flow path, in which droplets are back flowing, with laser 106. In this detection, both the droplet with fluorescence and the droplet without fluorescence are distinguished and counted. The detection of the droplets with fluorescence corresponds to the detection of the target DNA contained in the sample liquid. Further, the ratio of the number of droplets with fluorescence to the number of droplets without fluorescence indicates the density of the target DNA in the sample liquid. As described above, in order to detect the target DNA in the sample liquid, the three processes of droplet formation, gene amplification and detection can be performed in a single cartridge.

Figure 6:
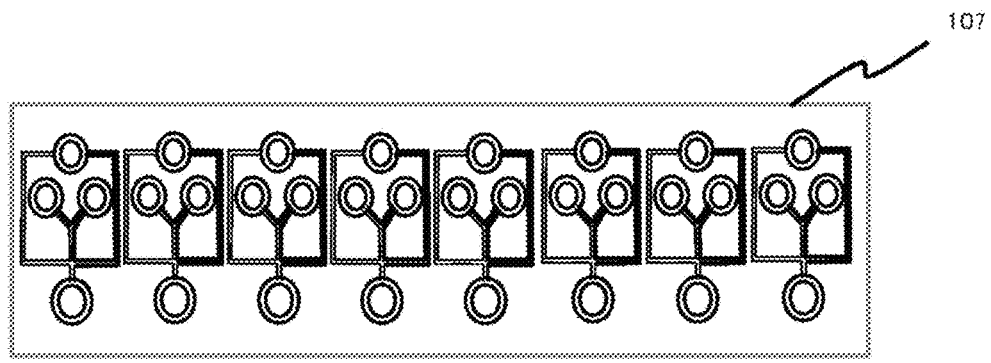
FIG. 6 is a view showing an interchangeable flow path cartridge for eight samples in which eight flow path patterns are formed in a micro flow path cartridge used in a reaction detector of the present invention.
Figure 7:
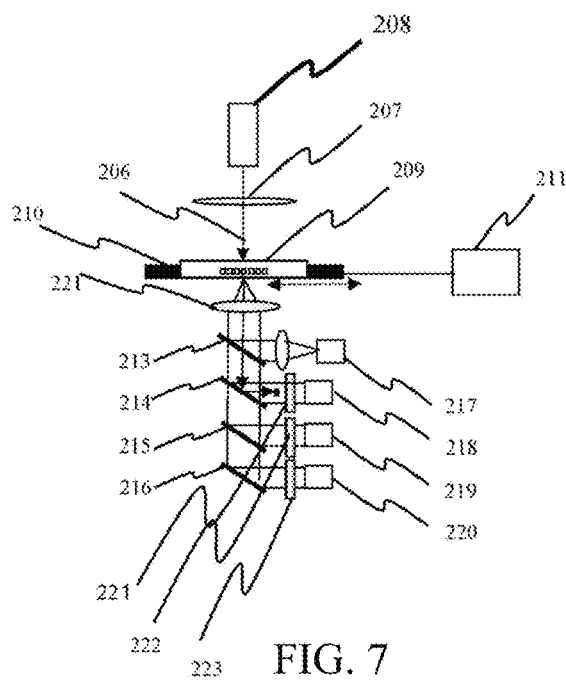
FIG. 7 is a view showing an outline of the configuration of a reaction detector using an interchangeable flow path cartridge for eight samples.
Figure 8:
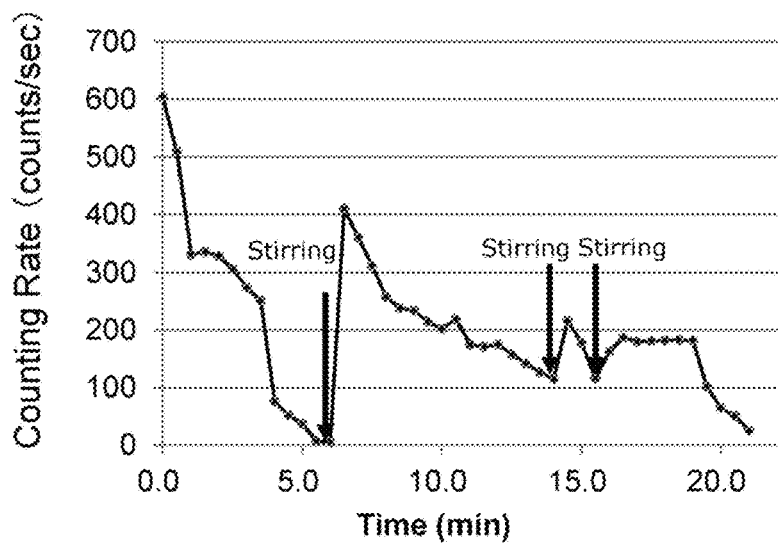
FIG. 8 is a graph showing the stirring effect by backflow in the apparatus for analyzing particles or apparatus for sorting particles of the present invention.

In order to improve the throughput of the above processing, a cartridge in which pluralities of flow path pattern shown in FIG. 5 are formed, is used. A chip capable of genetic testing of eight samples is shown in FIG. 6. The cartridge 107 in FIG. 6 has a structure in which eight flow path patterns shown in FIG. 5 are formed, and a single cartridge can be used to carry out an emulsion PCR method or emulsion isothermal amplification method for eight samples. The advantage of being able to process multiple samples with a single cartridge is that, in addition to reducing the operational cost per sample, test time may be shortened because multiple samples are processed simultaneously parallelly. This is because the emulsion formation and gene amplification reaction are processed simultaneously parallelly in the eight flow paths of a single cartridge, and only the final fluorescence detection process is a sequential inspection of the eight flow paths. This advantage is illustrated by the following equation. Assuming that the emulsion formation time is Et, the gene amplification reaction time is Dt, and the fluorescence detection time is Ft, the processing time per sample in the case of a single flow path cartridge is Et+Dt+Ft. On the other hand, in the case of an 8 flow paths cartridge, the processing time per sample is (Et+Dt)/8+Ft. That is, the emulsion formation time and the gene amplification time are reduced by a factor of 8. The processing time to form 1 million emulsions is 20 minutes, and the gene amplification reaction time is 30 minutes. If the detection rate of fluorescence is set to 1000 droplets/sec, the processing time for fluorescence detection in the emulsion is 16.6 minutes per flow path. Thus, in the case of eight flow paths, the processing time is eight times, and the total processing time is about three hours. This processing time is for 1 million droplets, and for 100,000 droplets, it is 45 minutes. An apparatus for performing a test using this multi-sample cartridge is shown in FIG. 7. In the 8-sample flow path cartridge 209 of this apparatus, measurement is performed from the end flow path. When the measurement thereof is finished, the next flow path in the cartridge 209 is sequentially measured by moving the cartridge stage 210. In this apparatus, the formation function of an emulsion containing droplets in oil and the temperature control function for gene amplification reaction in the emulsion are processed parallelly in eight flow paths. Subsequently, in the step of back flowing the emulsion, flow cytometry measurement of the emulsion droplet is sequentially performed for each of the eight flow paths by moving the stage. That is, by moving the cartridge using the step-and-repeat method, each 8 light flow path is sequentially illuminated with a light beam having a size to illuminate only one flow path, and all eight flow paths are measured. The accuracy of the position of the flow path after movement is confirmed by performing image recognition to detect both sides of the flow path with camera 217. In each flow path, scattered light and fluorescence generated when individual droplets pass through the illumination region are separated by wavelength by dichroic mirrors 214, 215 and 216 and band pass filters 221, 222 and 223. The scattered light is detected by light detector 217, and the fluorescence is detected by light detectors 218 and 219. In the above case, only a laser with a wavelength of 488 nm may be used as the illuminating light source, and it may be used in combination with other wavelength laser light. As fluorescent dyes by 488 nm excitation, SyberGreen or EVAGreen, or TaqMan probes such as FAM having a wavelength in the range of 500 nm to 550 nm can be used. If a laser with a wavelength of 637 nm (output: 50 mW) is simultaneously mounted, Cy5 as a TaqMan probe can be used.

INDUSTRIAL APPLICABILITY

The object of the present invention is the use in medical applications where cross contamination between samples is not permitted. Specifically, in cancer immunotherapy, the target molecule of cancer cells attacked by immune cells is studied, and thus single cell expression analysis of cancer cells is important. Therefore, single cell dispensing technology for cancer cells is required. Further, in cancer diagnosis, it is important to make high-sensitivity detection of oncogenes contained in the blood of cancer patients.

Although the present invention has been described with reference to specific embodiments, various changes and modifications obvious to those skilled in the art are possible without departing from the scope of the appended claims.

REFERENCE SIGNS LIST

1 . . . Sample liquid;
2 . . . Upstream reservoir;
3 . . . Downstream reservoir;
4 . . . Flow path;
10 . . . Outer frame of interchangeable micro flow path cartridge;
11 . . . Sample reservoir (First reservoir);
12 . . . Sheath reservoir (Second reservoir);
13 . . . Main flow path and connection port of sample liquid;
14 . . . Partition wall of sample liquid and sheath solution
15L . . . Connection port with sheath flow path for sheath fluid on the left side;
15R . . . Connection port with sheath flow path for sheath fluid on the right side;
16 . . . Sorting reservoir (Third reservoir);
17 . . . Collection reservoir (Third B reservoir);
18 . . . Connection port with sorting path of sorting reservoir;
19 . . . Connection port with sorting path of collection reservoir;
20 . . . Connection port with main flow path of discharged liquid;
21 . . . discharged liquid reservoir (Fourth reservoir);
22 . . . Main flow path (First flow path);
22-E . . . Main flow path (First flow path);
23L . . . Left sheath flow path (Second flow path);
23R . . . Right sheath flow path (Third flow path)
24L . . . Sorting flow path on push side of the pulse flow (Fourth flow path);
24R . . . Sorting flow path on pull side of the pulse flow (Fifth flow path)
35 . . . Illumination region;
70 . . . Multi-well plate of dispensing destination;
71 . . . Suspension of sample particles such as cells before dispensing in the container;
72 . . . Washing fluid in the container;
73 . . . Dispensing pipette (Transparent hollow pipe);
74 . . . pneumatic syringe pump;
75 . . . piston part of pneumatic syringe pump;
76 . . . Camera;
77 . . . Dispenser control PC;
78 . . . Particle dispenser;
80 . . . Well in multi-well plate;
81 . . . Liquid in well that has been pre-dispensed;
82 . . . Dispensing pipette;
83 . . . preliminary recognition area;
84 . . . recognition area;
85 . . . suspended particles;
86 . . . Piezo pump;
83 . . . Preliminary recognition area;
84 . . . Recognition area;
85 . . . Suspended particle;
86 . . . Piezoelectric;
87 . . . Sample liquid preparatory chamber;
88 . . . Parts to be exchanged for each sample liquid;
89 . . . Syringe pump;
90 . . . Droplets discharged from dispensing nozzle;
104 . . . Flow path;
102-1 . . . Sample reservoir;
102-2 . . . Reagent reservoir;
102-3 . . . Oil reservoir;
103-1 . . . Droplet reservoir;
106 . . . Laser illumination region;
107 . . . 8 samples compatible chip;
108 . . . Part held at a temperature of 65° C.;
208: Illumination light source;
206: Illumination light;
207: Lens;
209: Multi-sample flow path cartridge;
210: Cartridge stage;
211: Pulse motor driver for operation stage;
213: Beam sampler;
214: Dichroic mirror;
215: Dichroic mirror;
216: Dichroic mirror;
217: Camera;
218: Light detector;
219: Light detector;
220: Light detector;
300: $CO_2$ gas cylinder;
301: Pressure regulator;
302: Air filter;
303: Air pipe;
304: Perister pump;
305: Air tube pipe (for $CO_2$ gas inflow);
306: Air tube pipe (for $CO_2$ gas discharge);

307: Sample reservoir in the micro flow path cartridge (corresponding to 11 in FIG. 2);
308: Collection reservoir in the micro flow path cartridge (corresponding to 17 in FIG. 2);
309: Area of apparatus of cell sorter using micro flow path cartridge;
310: Chamber;
311: Cell sorter (may be a device that does not use a micro flow path cartridge or a device that uses it);
312: Area of micro flow path cartridge

The invention claimed is:

1. An apparatus for dispensing particles comprising a transparent hollow pipette for dispensing sample liquid containing particles, wherein the apparatus has
   a system for drawing up a sample liquid into the hollow pipette in each dispensing;
   a means for capturing two or more images of an entire dispensing sample liquid moving by gravity sedimentation in the hollow pipette;
   a controller for recognizing two or more shot images of time difference, distinguishing a substance moved by time difference from a substance unmoved by time difference in the image-captured substances in a whole of the entire dispensing sample liquid, and identifying the moved substance as a suspended particle; and
   a means for dispensing a sample liquid containing a target number of suspended particles.

2. The apparatus for dispensing particles according to claim 1, further comprising a means for forcibly moving the dispensing sample liquid in the hollow pipette.

3. The apparatus for dispensing particles according to claim 1, further comprising a means capable of controlling a gas atmosphere to a carbon dioxide gas atmosphere of 0.03 to 50%.

4. A method for dispensing particles, using a device for dispensing particles comprising a transparent hollow pipette for dispensing sample liquid containing particles, comprising the steps of:
   (1) drawing up a sample liquid into the hollow pipette in each dispensing;
   (2) image capturing two or more images of an entire dispensing sample liquid moving by gravity sedimentation in the hollow pipette,
   (3) recognizing two or more shot images of time difference, and distinguishing a substance moved by time difference from a substance unmoved by time difference in image-captured substances in a whole of the entire dispensing sample liquid, to identify the moved substance as a suspended particle; and
   (4) dispensing a sample liquid containing a target number of suspended particles.

5. The method for dispensing particles according to claim 4, wherein the device for dispensing particles further comprises a means for forcibly moving the dispensing sample liquid in the hollow pipette, and the dispensing sample liquid in the hollow pipette is image captured two or more times, before and after the dispensing sample liquid is moved by the means for forcibly moving the dispensing sample liquid in the image-capturing step (2).

6. The method for dispensing particles according to claim 4, wherein the device for dispensing particles further comprises means capable of controlling a gas atmosphere to a carbon dioxide gas atmosphere of 0.03 to 50%, and the steps (1) to (4) are performed in a 3-10% carbon dioxide gas atmosphere.

7. The method for dispensing particles according to claim 4, wherein the steps (1) to (4) are performed after a plurality of dispensable amounts of sample liquid are aspirated into a preparatory dispensing chamber located on the hollow pipette before the image capturing step (2) and a certain amount of sample liquid is supplied to the hollow pipette from the preparatory dispensing chamber, so as to dispense the dispensing sample liquid sequentially.

* * * * *